(12) United States Patent
Huber et al.

(10) Patent No.: US 8,596,142 B2
(45) Date of Patent: *Dec. 3, 2013

(54) VIBRATION-TYPE MEASURING TRANSDUCER

(75) Inventors: Christof Huber, Bern (CH); Vivek Kumar, Muttenz (CH); Christian Schutze, Basel (CH)

(73) Assignee: Endress + Hauser Flowtec AG, Reinach (CH)

( * ) Notice: Subject to any disclaimer, the term of this patent is extended or adjusted under 35 U.S.C. 154(b) by 382 days.
This patent is subject to a terminal disclaimer.

(21) Appl. No.: 12/805,304

(22) Filed: Jul. 23, 2010

(65) Prior Publication Data

US 2011/0016990 A1  Jan. 27, 2011

Related U.S. Application Data

(60) Provisional application No. 61/213,890, filed on Jul. 24, 2009.

(30) Foreign Application Priority Data

Jul. 24, 2009 (DE) .......................... 10 2009 028 006

(51) Int. Cl.
*G01F 1/84* (2006.01)
(52) U.S. Cl.
USPC ...................................................... 73/861.357
(58) Field of Classification Search
None
See application file for complete search history.

(56) References Cited

U.S. PATENT DOCUMENTS

| | | | |
|---|---|---|---|
| 4,823,613 A | | 4/1989 | Cage |
| 5,301,557 A | * | 4/1994 | Cage et al. ............... 73/861.355 |
| 5,497,666 A | | 3/1996 | Patten |
| 5,979,246 A | * | 11/1999 | Van Cleve et al. ........ 73/861.357 |
| 8,113,064 B2 | * | 2/2012 | Huber et al. ............. 73/861.357 |
| 2007/0034019 A1 | | 2/2007 | Doihara |

FOREIGN PATENT DOCUMENTS

| | | |
|---|---|---|
| DE | 35 05 166 A1 | 8/1986 |
| DE | 39 23 409 A1 | 1/1991 |
| DE | 695 15 576 T2 | 9/2000 |
| DE | 699 03 264 T2 | 7/2003 |

(Continued)

OTHER PUBLICATIONS

International Preliminary Examination Report dated Feb. 16, 2012.

*Primary Examiner* — Harshad R Patel
(74) *Attorney, Agent, or Firm* — Bacon & Thomas, PLLC

(57) ABSTRACT

A measuring transducer, comprises at least one measuring tube for conveying a flowing medium. The measuring tube vibrates at least at times during operation. The measuring transducer further comprises a sensor arrangement, which serves to register oscillations of the measuring tube. The measuring tube extends with an oscillatory length between an inlet-side, first measuring tube end and an outlet-side, second measuring tube end, and, during operation, oscillates about an oscillation axis, which is parallel to or coincides with an imagined connecting axis which imaginarily connects the two measuring tube ends. By means of a first oscillation sensor, which is arranged on the measuring tube, the sensor arrangement produces a first primary signal representing vibrations of the measuring tube, and by means of a second oscillation sensor, which is arranged on the measuring tube spaced from the first measuring sensor, the sensor arrangement produces a second primary signal representing vibrations of the measuring tube. The oscillation sensors of the sensor arrangement are placed in the measuring transducer in such a way that a measuring length of the measuring transducer corresponds to less than 65% especially less than 55% of the oscillatory length, and greater than 25%, especially greater than 30% of the oscillatory length.

66 Claims, 17 Drawing Sheets

(56) References Cited

FOREIGN PATENT DOCUMENTS

| DE | 699 38 581 T2 | 6/2009 |
| EP | 1 130 367 A1 | 9/2001 |
| EP | 1 790 955 A1 | 5/2007 |
| WO | WO 90/15310 | 12/1990 |
| WO | WO 99/40394 | 8/1999 |
| WO | WO 99/51946 | 10/1999 |

* cited by examiner

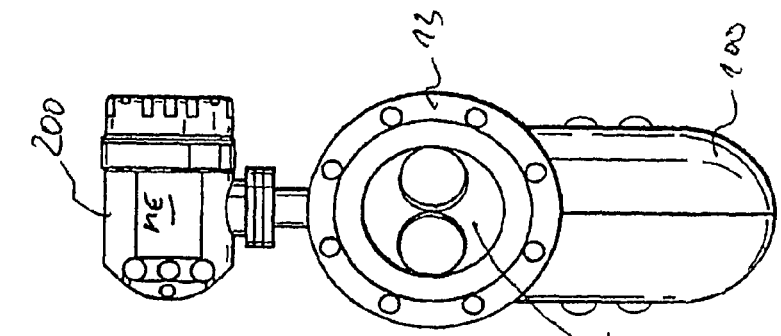
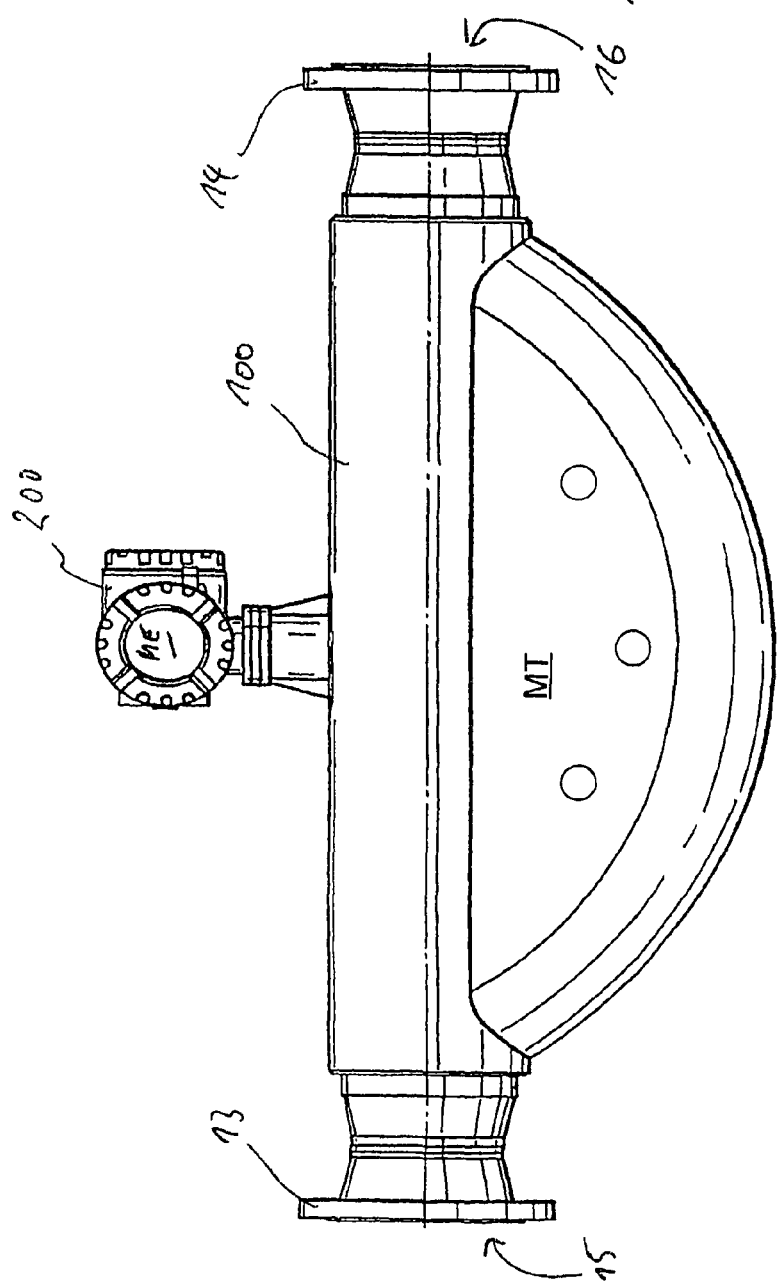

VIBRATION-TYPE MEASURING TRANSDUCER

CROSS-REFERENCE TO RELATED APPLICATION

This application is a Nonprovisional which claims the benefit of U.S. Application Provisional Application 61/213,890 filed on Jul. 24, 2009.

TECHNICAL FIELD

The invention relate to a vibration-type measuring transducer having: at least one measuring tube, which is used to conduct a flowing medium (for example a gas or a liquid), and which, in operation, oscillates about an oscillation axis, for instance in a bending oscillation mode; and a sensor arrangement, which serves to register the oscillations of the measuring tube, and which delivers primary signals representing vibrations of the at least one measuring tube. The invention furthermore relates to a measuring device for flowable media—embodied for example as a compact measuring devise and/or a Coriolis-mass flow-measuring device—having a measuring transducer as described, as well as measuring device electronics electrically coupled with the measuring transducer for processing the primary signals delivered by measuring transducer and for producing measured values.

BACKGROUND DISCUSSION

In industrial measurements technology (especially in connection with the regulating and monitoring of automated processes), in order to ascertain characteristic measurement variables of flowing media (for example liquids and/or gasses) in a process line (for example a pipeline), measuring systems are often used which—by means of a vibration-type measuring transducer and connected measuring device electronics (usually situated in a separate electronics housing) with a driver- and evaluating circuit—induce reaction forces (for example Coriolis forces) in flowing media and produce, derived from these forces, a measurement signal correspondingly representing the at least one measured variable (for example a mass flow rate, a density, a viscosity or other process parameter).

Measuring systems of this sort (often formed by means of an in-line measuring device of a compact design with an integrated measuring transducer, for instance a Coriolis mass flow meter) have long been known and have proved themselves in industrial use. Examples of measuring systems with a vibration-type measuring transducer as well as individual components thereof, are described, for example, in EP-A 317 340, EP-A 848 234, the JP-A 8-136311, the JP-A 9-015015, US-A 2007/0119264, US-A 2007/0119265, US-A 2007/0151370, US-A 2007/0151371, US-A 2007/0186685, US-A 2008/0034893, US-A 2008/0141789, U.S. Pat. No. 4,738,144, U.S. Pat. No. 4,777,833, U.S. Pat. No. 4,777,833, U.S. Pat. No. 4,801,897, U.S. Pat. No. 4,823,614, U.S. Pat. No. 4,879,911, U.S. Pat. No. 5,009,109, U.S. Pat. No. 5,024,104, U.S. Pat. No. 5,050,439, U.S. Pat. No. 5,291,792, U.S. Pat. No. 5,301,557, U.S. Pat. No. 5,398,554, U.S. Pat. No. 5,734,112, U.S. Pat. No. 5,476,013, U.S. Pat. No. 5,531,126, U.S. Pat. No. 5,602,345, U.S. Pat. No. 5,691,485, U.S. Pat. No. 5,796,010, U.S. Pat. No. 5,731,527, U.S. Pat. No. 5,796,011, U.S. Pat. No. 5,796,012, U.S. Pat. No. 5,804,741, U.S. Pat. No. 5,869,770, U.S. Pat. No. 5,945,609, U.S. Pat. No. 5,979,246, U.S. Pat. No. 6,047,457, U.S. Pat. No. 6,092,429, U.S. Pat. No. 6,073,495, U.S. Pat. No. 6,311,136, U.S. Pat. No. 6,223,605, U.S. Pat. No. 6,330,832, U.S. Pat. No. 6,397,685, U.S. Pat. No. 6,557,422, U.S. Pat. No. 6,651,513, U.S. Pat. No. 6,666,098, U.S. Pat. No. 6,691,583, U.S. Pat. No. 6,776,052, U.S. Pat. No. 6,799,476, U.S. Pat. No. 6,840,109, U.S. Pat. No. 6,883,387, U.S. Pat. No. 6,920,798, U.S. Pat. No. 7,017,424, U.S. Pat. No. 7,040,179, U.S. Pat. No. 7,073,396, U.S. Pat. No. 7,077,014, U.S. Pat. No. 7,080,564, U.S. Pat. No. 7,200,503, U.S. Pat. No. 7,216,550, U.S. Pat. No. 7,299,699, U.S. Pat. No. 7,318,356, U.S. Pat. No. 7,360,451, U.S. Pat. No. 7,392,709, WO-A 00 14 485, WO-A 01 02 816, WO-A 07/130024, WO-A 08/013545, WO-A 08/07 7574, WO-A 99/28708, WO-A 99 40 394 or WO-A 96/02812.

Each of the therein illustrated measuring transducers comprises at least one essentially straight or at least one curved (for example U or V-shaped) measuring tube (made, for example, of stainless steal, titanium, zirconium or tantalum) used for the conveyance of a medium (in certain cases, an extremely cold or extremely hot medium). For the purpose of generating oscillation forms in part influenced by the medium flowing through, during operation of the measuring system, the at least one measuring tube (extending with an oscillatory length between an inlet side, first measuring tube end and an outlet side, second measuring tube end) is caused to vibrate (especially in a bending oscillation mode) about an imagined oscillation axis imaginarily connecting the two ends.

For exciting oscillations of the at least one measuring tube, vibration-type measuring transducers consequently further exhibit an exciter mechanism, which is driven by an electric driver signal (e.g. a regulated electrical current) generated and correspondingly conditioned by the driver circuit of the measuring device electronics; and which—by means of at least one electromechanical (especially electrodynamic) oscillation exciter through which a current flows during operation and which acts practically directly on the measuring tube—excites mechanical oscillations (for example bending oscillations) in the at least one measuring tube, and, in this respect, converts the electrical power fed into the measuring transducer by the measuring electronics into mechanical movements. Moreover, measuring transducers of this sort include a sensor mechanism having at least two (especially electrodynamic and/or equally-embodied) oscillation sensors for at least point-specific registering of inlet-side and outlet-side oscillations (especially those in Coriolis mode) of the at least one measuring tube and for the production of electrical sensor signals, which serve as primary signals for the measuring transducer, and which are influenced by the process parameter to be registered, for instance the mass flow rate, the totaled mass flow or the density.

In the case of measuring transducers with curved (e.g. U, V or Ω-shaped) measuring tubes, for the oscillation form to be excited—the so-called driving or wanted mode—that particular oscillation form is normally chosen in which the measuring tube, in the case of a lowest natural resonance frequency, at least partially swings about an imaginary longitudinal axis of the measuring transducer in a pendulum-like fashion in the manner of a cantilever secured at one end; whereby Coriolis forces dependant on the mass flow are induced in the medium flowing through. These, in turn, lead to the fact that, in the case of a curved measuring tube and thus pendulum-like cantilever oscillations, bending oscillations of a frequency equal to the excited oscillations of the wanted mode are superimposed on the latter, according to at least a second, likewise natural oscillation form, the so-called Coriolis mode. In the case of measuring transducers with a curved measuring tube, these cantilever oscillations forced by the Coriolis forces in Coriolis mode normally correspond to that eigenoscillation form, in which the measuring tube also performs rotary oscillations about an imagined rotary oscillation axis aligned perpendicular to the longitudinal axis. Conversely, in the case of measuring transducers with straight measuring tubes, for the purpose of producing mass-flow-dependant Coriolis forces, a particular wanted mode is often chosen in which the measuring tube at least partially performs bending oscillations essentially in a single imaginary plane of oscillation, so that the oscillations in Coriolis mode are accordingly formed as bending oscillations coplanar to the wanted mode oscillations with an oscillation frequency equal to them. The two ends of the measuring tube are thus in this respect defined by those two particular oscillation nodes that are common to the wanted and Coriolis modes. In the case of a curved measuring tube, the oscillatory length therefore corresponds practically to a laid out straight length of an essentially freely oscillating section of the respective measuring tube, extending between the two oscillation nodes.

Due to the superimposition of the wanted and Coriolis modes, the inlet-side and outlet-side oscillations (which are registered by means of the sensor arrangement) of the vibrating measuring tube also exhibit a measurable phase difference, which is dependant on the mass flow. Normally, during operation, measuring tubes of this sort of measuring transducer (e.g. mass flow meters used in Coriolis) are excited to an instantaneous natural resonance frequency of the oscillation form chosen for the wanted mode, especially at an oscillation amplitude regulated to be constant. As this resonance frequency is, among other things, particularly dependent on the instantaneous density of the medium, the density of the medium, in addition to the mass flow; can be measured by means of a commercially available mass-flow meter. Furthermore, as shown in U.S. Pat. No. 6,651,513 or U.S. Pat. No. 7,080,564, it is also possible by means of a vibration-type measuring transducer to directly measure the viscosity of a medium flowing through, for example on the basis of an excitation power necessary for the excitation of the oscillations.

In the case of measuring transducers with two measuring tubes, the two measuring tubes are normally incorporated into the process line via an inlet-side distributor element extending between the measuring tubes and an inlet-side connecting flange, as well as via an outlet-side distributor element extending between the measuring tubes and an outlet-side connecting flange. In the case of measuring transducers with a single measuring tube, the latter normally communicates with the process line via an essentially straight connecting tube segment opening into the inlet-side, as well as via an essentially straight connecting tube segment opening into the outlet-side. Furthermore, each of the illustrated measuring transducers with a single measuring tube comprises at least a one-piece or multi-part embodied (for example tube, box or plate-shaped) counteroscillator, which is coupled to the measuring tube to form on the inlet side a first coupling zone and to form on the outlet side a second coupling zone; and which, during operation, essentially rests or oscillates opposite-equally, that is with equal frequency and opposite phase. The inner part of the measuring transducer, formed by means of the measuring tube and the counteroscillator, is normally held alone by means of the two connecting tube pieces, via which the measuring tube communicates with the process line during operation, in a measuring transducer housing, especially in a manner which makes possible the oscillations of the inner part relative to the measuring tube. In the case of the measuring transducers with a single, essentially straight measuring tube (as shown, for example U.S. Pat. No. 5,291,792, U.S. Pat. No. 5,796,010, U.S. Pat. No. 5,945,609, U.S. Pat. No. 7,077,014, US-A 2007/0119264, WO-A 01 02 816 or WO-A 99 40 394), the measuring tube and the counteroscillator are essentially arranged coaxially to each other, as is typical with traditional measuring transducers. In the case of those measuring transducers of the aforementioned type available on the market, the counteroscillator is normally also essentially tube-shaped and formed as an essentially straight, hollow cylinder, which is arranged in the measuring transducer in such a way that the measuring tube is at least partially jacketed by the counteroscillator. Comparatively inexpensive types of steel, for example structural steel or free-machining steel, are usually used as materials for such counteroscillators, even or especially in the case of the use of titanium, tantalum or zirconium for the measuring tube.

The exciter mechanism of measuring transducers of the type discussed here normally exhibits at least one electrodynamic oscillation exciter and/or at least one oscillation exciter that acts differentially upon the at least one measuring tube (and, in given cases, on the present counteroscillator or the present second measuring tube), while the sensor arrangement comprises an inlet-side, usually also electrodynamics oscillation sensor as well as at least one in essence equally embodied outlet-side oscillation sensor. Such electrodynamic and/or differential oscillation exciters of the vibration-type measuring transducers available on the market are normally formed by means of a magnet coil though at least part of which an electrical current flows (in the case of measurement transducers with one measuring tube and a counteroscillator coupled thereto, the magnet coil is usually fixed to counteroscillator), as well as by means of an elongated—especially rod-shaped—permanent magnet, which 1) serves as an armature, which 2) interacts with (and especially plunges into) the magnet coil, and which 3) is correspondingly fixed to the measuring tube to be moved. The permanent magnet and the magnet coil which is to serve as the exciter coil are normally arranged in such a way that they extend essentially coaxial to each other. Additionally, in traditional measuring transducers, the exciter mechanism is normally designed and placed in the measuring transducer in such a way that it in essence acts centrally on the at least one measuring tube. In such a case, the oscillation exciter—and, in this respect, the exciter mechanism—is normally fixed to the measuring tube at least pointwise along an imagined central peripheral line of the latter, as shown in the case of the measuring transducers proposed in U.S. Pat. No. 5,796,010, U.S. Pat. No. 6,840,109, U.S. Pat. No. 7,077,014 or U.S. Pat. No. 7,017,424.

In the case of most vibration-type measuring transducers available on the market, the oscillation sensors of the sensor arrangement are, as previously suggested, essentially of an equal construction to the oscillation exciter, at least insofar as they function according to the same principle of action. Consequently, the oscillation sensors of such a sensor arrangement are also in each case usually formed by means of an permanently magnetic armature (which is affixed to the measuring tube and which delivers a magnetic field), as well as by means of a coil which 1) interacts with the armature, which 2) is permeated by its magnetic field, which 3) at least at time supplied with an induced measurement voltage, and 4) which is normally affixed to the counteroscillator insofar as it is present, and otherwise affixed to one of the measuring tubes. Each of the aforementioned coils is additionally connected by means of at least one pair of electrical connecting lines to the mentioned operating and evaluation electronics. These lines most often run via the shortest route possible from the coils, over the counteroscillator, to the transducer housing.

The measuring device electronics of inline measuring devices of the aforementioned type normally available on the market most often exhibit a microcomputer—for example formed by means of a digital signal processor (DSP)—which delivers digital measured vales in real time. This microcomputer usually includes, in addition to at least one corresponding processor and associated circuit components (e.g. an A/D converter and a D/A converter), corresponding volatile and non-volatile data memories as well, for storing digital measurement and operation data ascertained internally or externally transmitted to the respective in-line measuring device, for instance for storing those chemical or physical properties relevant (for instance serving as a reference) to the measurement of the medium to be measured. In addition to the microcomputer and the driver circuit (which makes the operation of the measuring transducer possible), the measuring device electronics normally further exhibit an input circuit, which implements for the microcomputer the conditioning of the measurement signals delivered by the measuring transducer, and which (forming the aforementioned measurement and evaluating circuit of the measuring device electronics) is correspondingly interconnected with the microcomputer. Based upon the measurement signals delivered by the measuring transducer and/or upon the driver signals (which drive the measuring transducer) delivered by the measuring device electronics, the microcomputer ascertains the desired primary measured values—for instance an instantaneous mass flow rate of the medium flowing through the measuring transducer, and/or a totaled mass flow, which corresponds to a mass of the mediums which has, overall, flowed through the measuring transducer during a predetermined period of time—and provides these in real time.

Since conventional measuring systems of the type discussed are normally embodied as independent measuring devices which are to be incorporated (for example via a 2-wire or 4-wire line) into a superordinated electronic data processing system (for example a system which controls a filling process and/or one formed by means of a programmable logic controller (PLC)), the measuring device electronics of modern inline measuring devices of the type discussed in each case also exhibit a corresponding communication circuit, which makes possible the transmission and reception of measurement or operation data. This communication circuit occurs, for example, in the form of a digital output of the sort established in industrial measurements and automation technology, in the form of an established 4-20 mA electrical current signal output, in the form of a bus interface conforming to NAMUR recommendation NE43:1994 and/or to the PROFIBUS standard IEC 61158 or in the form of another interface circuit conforming to an industry standard. Additionally provided in the measuring device electronics is a supply circuit, which assures the supplying of the in-line measuring device with energy and which obtains the necessary energy from an internal energy storer and/or from the electronic data processing system via a 4-wire line or by means of a 2-wire line, the latter line for example embodied as a 4-20 mA current loop with measuring-device-side load modulation.

As can be drawn, among other things, from the previously mentioned EP-A 848 234 or WO-A 96/02812, in the case of a measuring system formed by means of a vibration-type measuring transducer, for the achievement of the desired—and no less expected—high accuracy of measurement, a particular meaning is to be ascribed to the positioning of the primary oscillation sensor relative to the chosen oscillation nodes of the oscillations of the measuring tube or measuring tubes excited for the purpose of measurement of the primary measured variable, mass flow. According to EP-A 848 234 or WO-A 99/28708, a lower sensitivity to disturbance variables (for instance from external vibrations)—and in this respect a high accuracy of measurement for the measuring system in question—would additionally be reachable by placing the oscillation sensors in each case as near as possible to the oscillation nodes of the previously mentioned wanted mode, whereby its share of the oscillations registered by means of the sensor arrangement—and in this respect of the respective primary signal—is kept as low as possible. In the case of conventional measuring systems of the type discussed which are available on the market, especially in the case of those solely with oscillation exciters acting centrally on the measuring tube, for the purpose of achieving as high a sensitivity as possibly to the primary measured variables (especially the mass flow or mass flow rate), with, simultaneously, a lowest possible sensitivity to possible disturbance variables, as well as a sufficiently high signal-to-noise ratio for the primary signal in the area of the excited oscillation frequency, the oscillation sensors of the sensor mechanism are placed in the measuring transducer in such a way that a measuring length of the measuring transducer corresponding to a length of a region of the measuring tube extending between the first oscillation sensor and second oscillation sensor amounts to more that 65% of the oscillatory length. In the case of a curved measuring tube, the measuring length then corresponds to a laid out straight length of the essentially freely oscillating section of the respective measuring tube extending between the two oscillation sensors.

Investigations of various measuring systems of the type discussed here have, however, shown that a disadvantage of positioning the oscillation sensors in the aforementioned manner exists in the fact that, for achieving an oscillation amplitude of 10-15 μm at the site of the oscillation sensors sufficient for the desired high accuracy of measurement, maximum oscillation amplitudes relatively large for the respective measuring system of about 30 μm at the center of the measuring tube are necessary for the excited oscillations in the wanted mode. In association therewith, a relatively high electrical power, in some cases amounting to far greater than 100 mW, must be converted in the exciter mechanism, this being especially true in the case of low mass flow rates.

Not least of all in the case of in-line measuring devices (as for example is proposed in the previously mentioned U.S. Pat. No. 6,799,476 or U.S. Pat. No. 7,200,503) whose measuring device electronics are, during operation, to be connected with a superordinated data processing system solely by means of a 2-wire connection (for example a 4-20 mA current loop) serving both the measured data and the energy transfer, both the continually available as well as the maximum allowable electrical power is, as is known, limited (depending on the voltage supply used or allowed from a technical safety point of view), to about 40-150 mW or to 1 W, depending on the particular case, so that, among other things, sufficient energy is not always available during operation to allow for the provision of the signal-to-noise ratio or the noise separation actually required. For the case mentioned—in which the in-line measuring device is, by means of a 4-20 mA current loop, both externally supplied with energy and also provided with the measured values by adjusting the electrical current level flowing through the current loop proportionally thereto—the less electrical power becomes available to the measuring system overall (and in this respect the less electrical exciter power becomes available to the measuring transducer), the more power such would actually be necessary for the desired high measurement of accuracy.

Moreover, an additional disadvantage of a higher maximum oscillation amplitude exists in the fact that a multiplied degree of unwanted, disturbing vibrations can be provoked, and as a result, the measurement system's overall susceptibility to disturbance is correspondingly increased.

SUMMARY OF THE INVENTION

An object of the invention is, consequently, to improve among vibration-type measuring transducers the efficiency with which, during operation, electrical excitation power or excitation energy fed into their respective exciter mechanisms is ultimately changed into primary signals, and to do so in such a way that, on one hand, the primary signals (especially their respective signal components representing the Coriolis mode) exhibit at as small maximum oscillation amplitudes of the measuring tube as possible—and, as a consequence of this, at low electrical excitation power—as high a signal-to-noise ratio as possible; and, on the other hand, that the sensor arrangement (and in this respect also the measuring transducer overall) exhibit a sufficiently high sensitivity to the primary measured variables to be registered, especially the mass flow rate and/or the totaled mass flow.

For achieving this object, the invention resides in a vibration-type measuring transducer, which comprises:
  at least one measuring tube for the conveyance of a flowing medium (for example a gas and/or liquid), which extends with an oscillation length between an inlet-side first measuring tube end and an outlet-side second measuring tube end, and during operation oscillates (for example in a bending oscillation mode) about an imagined oscillation axis parallel to or coinciding with an imagined connecting axis which imaginarily connects the two ends of the measuring tube; as well as
  a sensor arrangement which serves to register the oscillations of the measuring tube, with 1) a (for example electrodynamic) oscillation sensor which is arranged on the measuring tube (for example on inlet side), and which delivers a first primary signal of the measuring transducer representing a vibration of the measuring tube, and 2) a second (for example electromagnetic) oscillation sensor which is arranged on the measuring tube spaced at a distance from the first oscillation sensor (for example on the outlet-side), and which delivers (especially simultaneously with the first primary signal) a second primary signal of the measuring transducer representing the vibrations of the measuring tube. The first oscillation sensor of the sensor arrangement and the second oscillation sensor of the sensor arrangement are furthermore placed in the measuring transducer in such a way, that a measuring length of the measuring transducer (corresponding to a length of a region extending between the first and second oscillation sensors) also corresponds to less than 65% (preferably less than 55%) of the oscillation length, and greater than 25% (preferably greater than 30%) of the oscillation length.

The invention moreover resides in a measuring device (for example embodied as a compact measuring device or Coriolis mass flow measuring device) for flowable—especially fluid—media, which comprises a measuring transducer as above as well as a measuring device electronics electrically coupled with said measuring transducer for processing primary signals delivered by the measuring transducer, and for producing measured values.

According to a first embodiment of the measuring transducer of the invention, the at least one measuring tube is embodied in a partially curved or especially arc-shaped fashion, especially inside the region extending between the first oscillation sensor and the second oscillation sensor.

According to a second embodiment of the measuring transducer of the invention, it is provided that the measuring tube is designed in an essentially V-shaped fashion, at least inside the region extending between the first oscillation sensor and the second oscillation sensor.

According to a third embodiment of the measuring transducer of the invention, it is provided that the measuring tube exhibits a caliber that amounts to greater than 1 mm (especially greater than 5 mm). Developing this embodiment of the invention further, it is additionally particularly provided that the caliber of the measuring tube amounts to more that 50 mm (also, for example, greater than 60 mm), and that the measuring length of the measuring transducer corresponds to less than 65% of the oscillation length. Alternatively, the caliber of the measuring tube can amount to greater than 15 mm (also, for example, greater than 20 mm) and/or amount to less than 50 mm (also, for example, less than 40 mm), and the measuring length of the measuring transducer then corresponds to less than 55% of the oscillation length. In particular, the first measuring tube can advantageously be dimensioned in such a way and the oscillation sensors positioned in such a way that a measuring-length to caliber ratio of the measuring transducer (defined by a ratio of the measurement length of the measuring transducer to the caliber of the measuring tube) is smaller than 10, and especially smaller than 5.

According to a fourth embodiment of the measuring transducer of the invention, it is provided that the measuring tube exhibits 1) an inlet-side, first straight tube segment with an imaginary longitudinal axis having a direction vector pointing toward the first coupling zone, and 2) an outlet-side, second straight tube segment with an imaginary longitudinal axis having a direction vector pointing toward the second coupling zone; and that the two straight sections of tube are arranged together in such a way (for example forming an in essence at least partially V-shaped or U-shaped measuring tube) that the direction vector of the imaginary longitudinal axis of the first straight tube segment and the direction vector of the imaginary longitudinal axis of the second straight tube segment intersect to form an angle, especially an angle amounting to less than 170° (also, for example, less than 160°), and/or greater than 10° (also, for example, greater than 20°). At least in the case where said angle amounts to less than 100°, it is further provided that the first oscillation sensor of the sensor arrangement and the second oscillation sensor of the sensor arrangement are placed in the measuring transducer in such a way that a measuring-length to oscillation-length ratio (defined by a ratio of the measuring length to the oscillation length) is smaller than or equal to 0.6, and especially in such a way that the measuring-length to oscillation-length ratio is greater than 0.3. At least in the case where said angle amounts to greater than 100° (also, for instance, greater than 115°), it is further provided that the first oscillation sensor of the sensor arrangement and the second oscillation sensor of the sensor arrangement are placed in the measuring transducer in such a way, that the measuring-length to oscillation-length ratio is smaller than or equal to 0.062, and especially in such a way that the measuring-length to oscillation-length ratio is greater than 0.045.

Developing the fourth embodiment of the invention further, it is additionally provided that the two straight sections of tube are connected to each other by means of a curved (for example arc-shaped) tube segment, especially in such a way that the arc-shaped tube segment exhibits an average tube arc radius R measured from its central line, which amounts to less than 500 mm (also, for example, less than 300 mm) and that the measuring tube, or at least its arc-shaped segment, exhibits a tube wall thickness that amounts to less than 7 mm (also, for example, less than 3 mm). In advantageous manner, the first measuring tube is also dimensioned in such a way, that the areal moment of inertia of a cross section of the measuring tube amounts to at least 40 mm$^4$ (also, for example, greater than 150 mm$^4$), especially in such a way that an areal moment of inertia to measuring-length ratio $I_{10}/L_{50}$ of the measuring tube, defined by a ratio of said areal moment of inertia to the measuring length of the measuring tube, amounts to greater than 40 mm$^3$ (also, for example, greater than 150 mm$^3$). Alternatively or in addition to this, the arc-shaped tube segment can furthermore also be embodied in such a way, that a tube arc radius to tube outer radius ratio, defined by a ratio of the tube arc radius to a tube outer radius of the arc-shaped tube segment, amounts to less than 60 (also, for example, less than 50) and/or greater than 3 (also, for example, greater than 4), and this especially in the case that the first oscillation sensor of the sensor arrangement and the second oscillation sensor of the sensor arrangement are placed in the measuring transducer in such a way, that a measuring-length to oscillation-length ratio, defined by a ratio of the measuring length to the oscillation length, is greater than 4.0

According to a fifth embodiment of the measuring transducer of the invention, it is provided that the first oscillation sensor and the second oscillation sensor are of equal construction to each another.

According to a sixth embodiment of the measuring transducer of the invention, such further comprises a counteroscillator (especially one which, during operation, oscillates essentially opposite phase to the measuring tube and/or is arranged parallel to it) which is affixed to the measuring tube to form on the inlet side a first coupling zone and affixed to the measuring tube to form on the outlet side a second coupling zone; wherein the first coupling zone defines an inlet-side, first end of the measuring tube, and the second coupling zone defines an outlet-side, second end of the measuring tube. Further developing this embodiment of the invention, it is additionally provided that both the first oscillation sensor and the second oscillation sensor are placed in the measuring transducer in such a way that each of the oscillation sensors (for example predominantly or exclusively) registers (for example differentially) oscillations of the measuring tube relative to the counteroscillator; and/or that the measuring tube and counteroscillator oscillate during operation at least at a common oscillation frequency with opposite phase relative to one other; and/or that both the first primary signal and the second primary signal represent (for example opposite-equal) oscillatory movements of the at least one measuring tube relative to the counteroscillator; and/or that the oscillation sensors (and/or equally embodied ones) register (for example simultaneously or differentially) vibrations of the at least one (and/or the U- or V-shaped) measuring tube and those of the (and/or the U- or V-shaped) counteroscillator.

According to a seventh embodiment of the measuring transducer of the invention, it is provided that the first oscillation sensor is placed in the measuring transducer spaced as equally distant from the center of the measuring tube as the second oscillation sensor is.

According to an eighth embodiment of the measuring transducer of the invention, such additionally includes two measuring tubes which, for example, oscillate essentially opposite phase to each other during operation and/or which are parallel to each other and/or which are equally embodied as regards shape and material, and which, forming a first coupling zone on the inlet-side, are mechanically connected to each other by means of a (for example plate-shaped) first coupling element, and, forming a second coupling zone on the outlet-side, by means of a (for example platform shaped) second coupling element, wherein the first coupling zone in each case defines an inlet-side, first end of each of the measuring tubes; and the second coupling zone in each case defines an outlet-side, second end of each of the measuring tubes. Developing this embodiment of the invention further, it is additionally particularly provided that each of the two measuring tubes in each case communicates on the inlet-side with a first distributor element of the measuring transducer, and in each case on the outlet-side with a second distributor element of the measuring transducer. Alternatively or in addition to this, it is further provided in this embodiment of the invention that during operation, the two measuring tubes oscillate at least at a common oscillation frequency with opposite phase to each other, and/or that both the first primary signal of the measuring transducer (delivered by the first oscillation sensor) as well as the second primary signal of the measuring transducer (delivered by the second oscillation sensor) represent oscillations of the measuring tubes relative to each other, for example oscillations of the measuring tubes which are of opposite-phase relative to each other.

According to a ninth embodiment of the measuring transducer of the invention, such further includes—for causing the vibration of the at least one measuring tube, for example in a bending oscillation mode in which it at least partially executes bending oscillations about the imagined oscillation axis—an exciter mechanism, which exhibits at least one (especially exactly one) for example electrodynamic oscillation exciter, which acts (for example in the region of half the oscillation length) upon the measuring tube. Developing this embodiment of the invention further, it is additionally particularly provided that, during operation, the at least one measuring tube is at least at times excited in the wanted mode by means of the exciter mechanism, in that it (for example predominantly or exclusively) performs bending oscillations about the imagined oscillation axis (for example with a single and/or with a lowest resonance frequency of the measuring tube), in particular in such a way that each of the primary signals of the measuring transducer in each case exhibits a signal component (for example dominating and/or corresponding with the wanted mode,) with a signal frequency, for example, corresponding to the bending oscillation in the wanted mode and/or corresponding to a (for example lowest) resonance frequency of the at least one measuring tube. Alternatively or in addition to this, it is additionally provided in this embodiment of the invention that the first oscillation sensor is placed in the measuring transducer spaced as equally distant from the at least one oscillation exciter as the second oscillation sensor is.

According to a tenth embodiment of the measuring transducer of the invention, it is provided that the measuring tube is made of metal, in particular at least partially of stainless steel, titanium, tantalum or zirconium.

According to an eleventh embodiment of the measuring transducer of the invention, it is provided that the sensor arrangement otherwise exhibits no further oscillation sensors beyond the first and second oscillation sensors.

According to a first embodiment of the measuring device of the invention, it is provided that the measuring device electronics, both by means of the first primary signal and by means of the second primary signal—in particular based on a phase difference existing between the first primary signal and the second primary signal—at least at times generates a mass flow measured value instantaneously representing a mass flow rate, m, of medium flowing through the measuring transducer.

According to a second embodiment of the measuring device of the invention, it is provided that during operation, the measuring device electronics recurringly produces a phase difference value which represents the phase difference existing instantaneously between the first primary signal and the second primary signal.

According to a third embodiment of the measuring device of the invention, such further includes a driver circuit (especially one which communicates with the evaluating circuit during operation), which is electrically coupled with the measuring transducer, and which delivers at least one exciter signal driving its exciter mechanism.

According to a fourth embodiment of the measuring device of the invention, it is provided that the measuring device electronics is, by means of a two-wire connection (particularly embodied as a 4-20 mA current loop), electrically connectable with an external, electronic, data processing system.

According to a fifth embodiment of the measuring transducer of the invention, it is provided that, by means of at least one of the primary signals, the evaluating circuit at least at times generates a density measured value (in particular a digital one), which represents an instantaneous density, ρ, of the medium flowing through the measuring transducer.

According to a sixth embodiment of the measuring transducer of the invention, it is provided that, by means of at least one of the primary signals, the evaluating circuit at least at times generates a viscosity measured value (in particular a digital one), which represents an instantaneous viscosity, η, of the medium flowing through the measuring transducer.

A fundamental idea of the invention lies in placing the oscillation sensors—which serve to point-specifically register the oscillatory movements of the at least one measuring tube, in particular the oscillations in Coriolis mode—closer to the site of maximum oscillation amplitude of the oscillations of the wanted mode—that is nearer to the at least one oscillation exciter or nearer to the half-length of the at least one measuring tube—in order to thereby achieve a good compromise between, on one hand, a sufficiently high sensitivity with which each of the measured variables to be registered (for instance the mass flow rate) for the medium flowing through the measuring transducer is ultimately converted into a corresponding signal variable of the respective primary signals, e.g. a signal amplitude, a signal difference and/or a phase angle, or a phase difference between the two primary signals and, on the other hand, a sufficiently high signal-to-noise ration of the primary signals of the measuring transducer. The invention is, in this case, based on the surprising recognition that a high sensitivity—achievable through a high measuring length—is not alone decisively responsible for the accuracy of measurement of measurement systems of the type in question, but rather also, in particular, as high a signal amplitude for the primary signals as possible—achievable through as low a measuring length as possible. As a result of this, an optimal measuring length for vibration-type measuring transducers is achieved when a certain product is overall as maximum as possible, which product is formed from an actual sensitivity $S_{ACT}$ of the measuring transducer, relative to a (theoretical) maximum possible sensitivity $S_{MAX}$—that is that sensitivity at maximum measuring length (identical with the oscillatory length of the measuring tube)—and a signal amplitude $A_{ACT}$ of the primary signals at the site of the oscillation sensors that is actually achievable during operation, relative to a (theoretical) maximum possible signal amplitude $A_{MAX}$ at the site of the maximum oscillation amplitude—thus typically in the region of the oscillation exciter or in the region of half the oscillatory length—so that as a result, the condition:

$$\Re = \frac{A_{ACT}}{A_{MAX}} \cdot \frac{S_{ACT}}{S_{MAX}} \stackrel{!}{=} \text{Max}$$

is fulfilled, i.e., the function $\Re$ is maximized or at least approaches maximum.

An advantage of the inventions lies, among other things, in the fact that even when largely maintaining established circuit architectures and technologies for measured signal conditioning and evaluating, an extremely accurate measuring of the mass flow, e.g. the mass flow rate, is made possible even with an extremely low excitation power and/or at very low mass flow rates. As a result of this, the measuring range of the measuring system of the type discussed can be, as a whole, widened. An additional advantage of the measuring transducer according to the invention can further be seen in the fact that it is especially suitable for use in measuring systems with low power levels of less than 1 W and/or those operated by means of a 4-20 mA current loop.

BRIEF DESCRIPTION OF THE DRAWING

The invention, as well as additional advantageous embodiments thereof, will now be explained more closely by means of examples of embodiments presented in the figures of the appended drawing. Identical parts are provided with the same reference characters in all figures; when demanded for reasons of clarity of overview or when it otherwise appears necessary, previously mentioned reference characters are omitted in subsequent figures. Additional advantageous embodiments or further developments—in particular combinations of partial aspects of the invention which are at first only individually explained—will further become evident from the figures of the drawing, as well as from the dependant claims per se. The figures show as follows:

FIGS. 2a, 2b in different side views, a further variant of a measuring system embodied as a compact measuring device for media flowing in pipelines;

DETAILED DISCUSSION IN CONJUNCTION WITH THE DRAWINGS

Figure 1B:
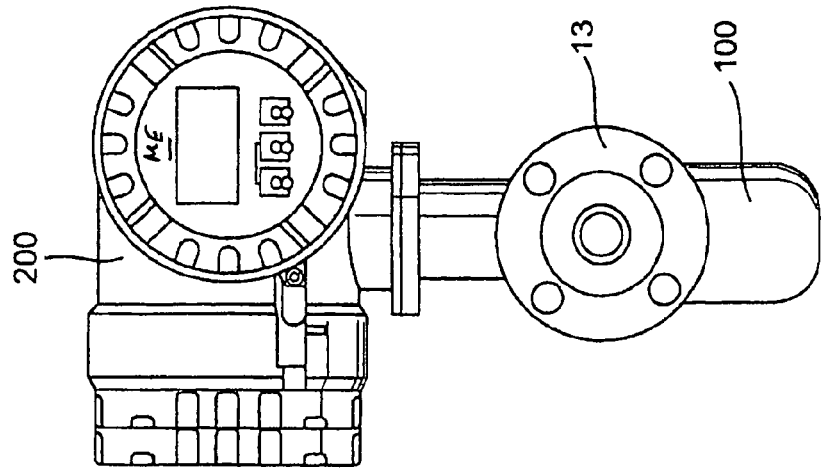
FIGS. 1a, 1b in different side views, a variant of a measuring system embodied as a compact measuring device for media flowing in pipelines.
Figure 1A:
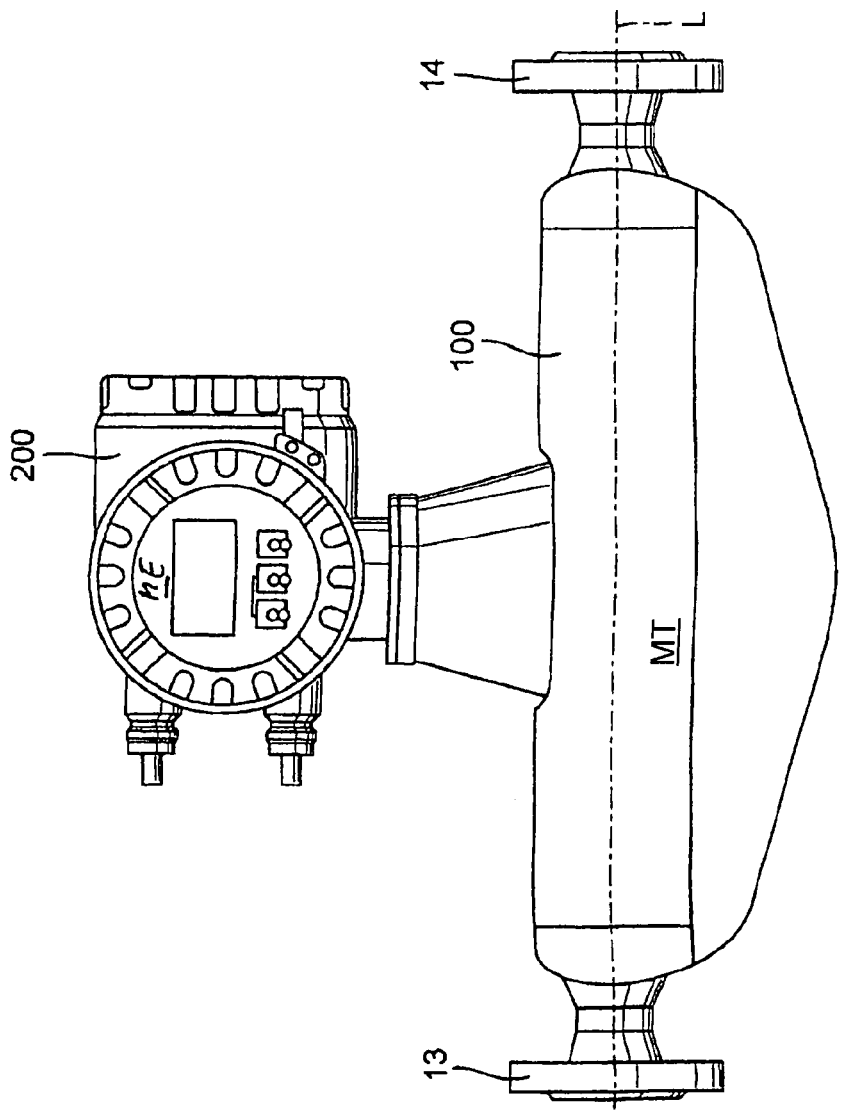
Figure 3:
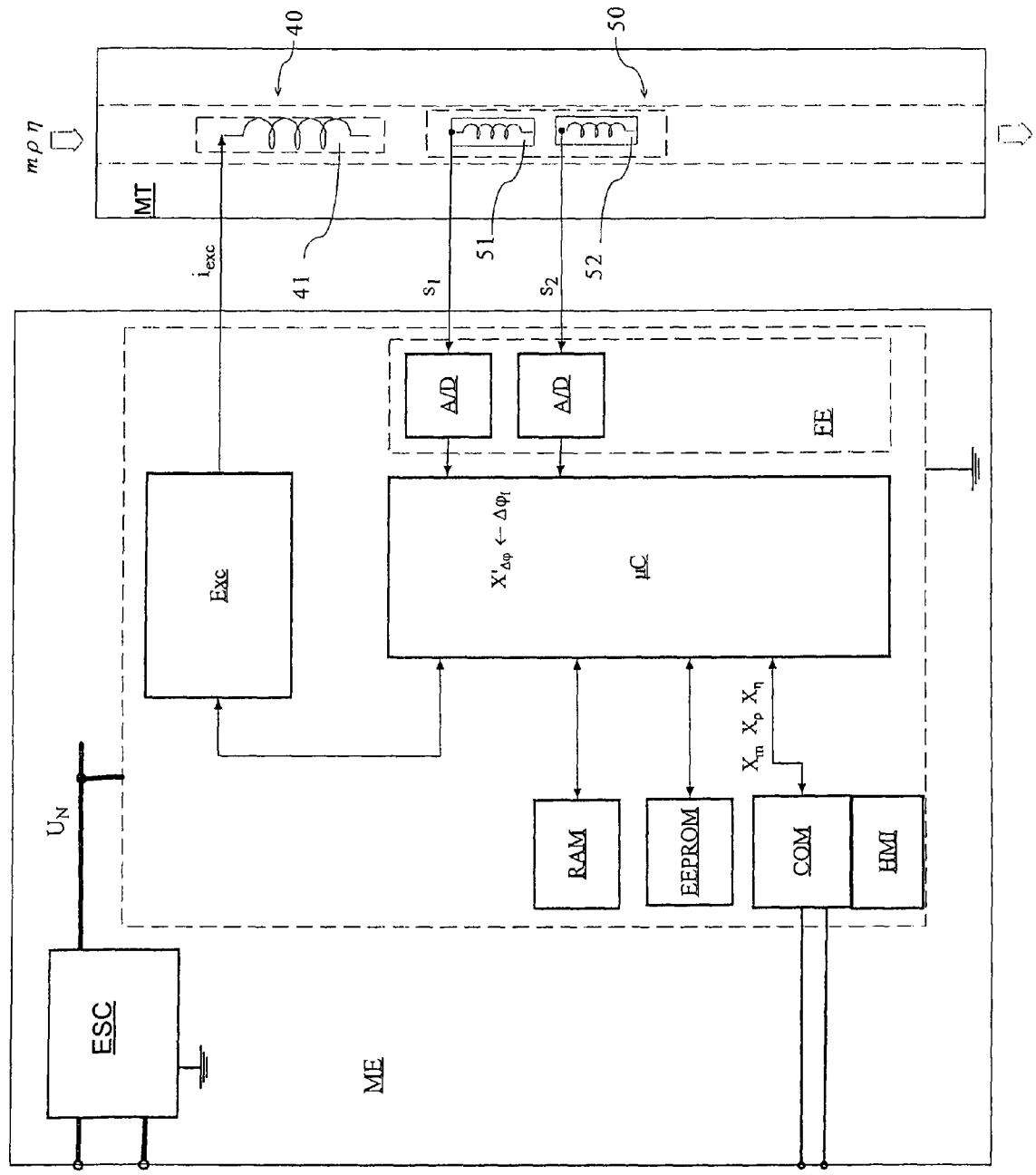
FIG. 3 schematically in the manner of a block diagram, a measuring device electronics—in particular suited for a measuring system according to the FIGS. 1a, 1b, 2a, 2b—with a connected vibration-type measuring transducer.

FIGS. 1a, 1b and FIGS. 2a, 2b, respectively, show variants of a measuring system for flowable, especially liquid, media. The measuring system is insertable into a process line (not shown), for example a pipeline of an industrial facility, and serves, in particular, to measure and or monitor a least one physical, measured variable of a medium flowing through the process line, for instance a mass flow, a density, a viscosity, a pressure, etc. The measuring system—implemented here as an in-line measuring device of compact construction—thus comprises a vibration type measuring transducer MT, which is connected to the process line via an inlet-side end as well as an outlet-side end. During operation, medium to be measured (for example a low-viscosity liquid and/or a high-viscosity paste and/or a gas) flows through the measuring transducer. The measuring transducer is connected to the measuring device electronics ME of the measuring system. The measuring device electronics ME is supplied, especially during operation, with electrical energy from the exterior via a connecting cable and/or by means of an internal energy storer. The measuring device electronics includes, as is schematically represented in FIG. 3 in the manner of a block diagram, a driver circuit Exc, which serves to drive the measuring transducer, as well as an evaluating circuit μC, which processes the primary signals of the measuring transducer MT. The evaluating circuit is formed, for example, by means of a microcomputer and/or communicates with the driver circuit Exc. During operation, the ealuating circuit delivers at least one measured value representing a measured variable (for example the instantaneous or totaled mass flow). The driver circuit Exc and the evaluating circuit μC as well as other electronic components of the measuring device electronics which serve the operation of the measuring system—for instance the internal energy supply circuits ESC supplying internal supply voltages $U_N$, and/or a communication circuit COM for the connection with a superordinated measurement data processing system and/or a fieldbus—are furthermore accommodated in a corresponding electronics housing 200 (especially one embodied in impact and/or explosion-resistant, hermetically sealed fashion). For visualization of measured values produced internally in the measuring system and/or in given cases status reports generated internally in the measuring system (for example an error report or an alarm), the measuring system can moreover exhibit onsite a display and interacting element HMI—for instance an LCD or TFT display placed in an electronics housing behind a window correspondingly provided therein, as well as a corresponding input keypad and/or touch screen—which at least at times communicates with the measuring device electronics. Advantageously, the (especially programmable and/or remotely parameterable) measuring device electronics can furthermore be designed in such a way that during operation of the in-line measuring device it can exchange with one of these superordinated data processing systems (for example a programmable logic controller (PLC), a personal computer and/or a workstation), via a data transmission system, for example a fieldbus system and/or wirelessly via radio, measuring and or other operating data (for instance current measured values or setting and/or diagnostic values for the control of the in-line measuring device). In such a case, the measuring device electronics ME can, for example, exhibit an internal energy supply circuit ESC of a sort which, during operation, is fed (via the aforementioned fieldbus system) by an external energy supply provided in the data processing system. According to one embodiment of the invention, the measuring device electronics is furthermore embodied in such a way that, by means of a two-wire connection 2L (configured, for example, as a 4-20 mA current loop), it is connectable with the external electronic data processing system, and through this is provided with electrical energy and can transmit measured values to the data processing system. In the case in which the in-line measuring device is to be equipped for coupling to a fieldbus or other communication system, the measuring device electronics ME can exhibit a corresponding communication interface COM for data communication according to one of the relevant industry standards. The electrical connection of the measuring transducer to the aforementioned measuring device electronics can occur by means of corresponding connecting lines, which lead out from the electronics housing 200 (for example via cable feed-through), and are at least sectionally laid inside of the transducer housing. The connecting lines can, in such a case, be at least partially embodied as electrical line wires which are at least sectionally encased in electrical insulation, e.g. in the form of "twisted pair" lines, flat ribbon cables and/or coaxial cables. Alternatively or in addition to this, the connecting lines can also be at least sectionally formed by means of a circuit board (especially a flexible circuit board, as the case may be, a lacquered one); compare the previously mentioned U.S. Pat. No. 6,711,958 or U.S. Pat. No. 5,349,872.

In FIGS. 4 and 5, and 6 and 7, respectively, for further explanation of the invention, first and second examples of embodiments of a vibration-type measuring transducer suitable for the implementation of the measuring system are schematically represented. The measuring transducer MT generally serves to produce in a medium flowing through it (for instance a gas and/or a liquid) mechanical reaction forces (e.g. mass-flow-dependent Coriolis forces, density-dependent inertial forces and/or viscosity-dependent frictional forces), which react upon the measuring transducer in a measurable manner, especially a manner registerable via sensor. Derived from these reaction forces, for example, a mass flow m, a density ρ and/or a viscosity η of the medium can be measured. For this, each of the measuring transducers includes in each case an inner part, which is arranged in a transducer housing 100, and which actually effects the physical-electrical transducing of the at least one parameter to be measured. Additionally to accommodation of the inner part, the transducer housing 100 can furthermore serve to hold the electronics housing 200 of the in-line measuring device. The driver and evaluating circuit are accommodated in the electronics housing.

Figure 4:
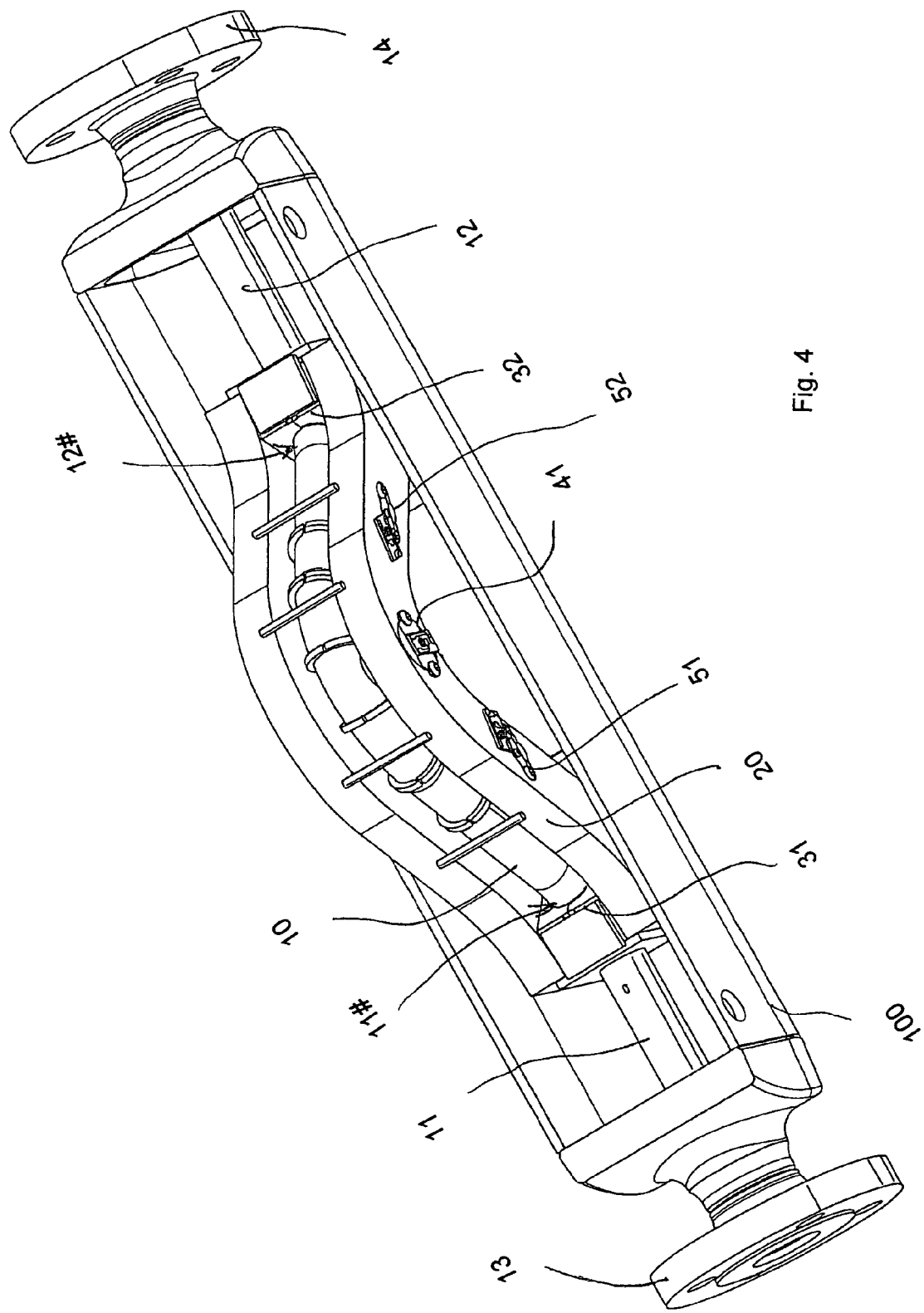
FIGS. 4, and 5 respectively, in partially sectioned and perspective views, a variant of a vibration-type measuring transducer, particularly suited for a measuring system according to FIGS. 1a, 1b.
Figure 5:
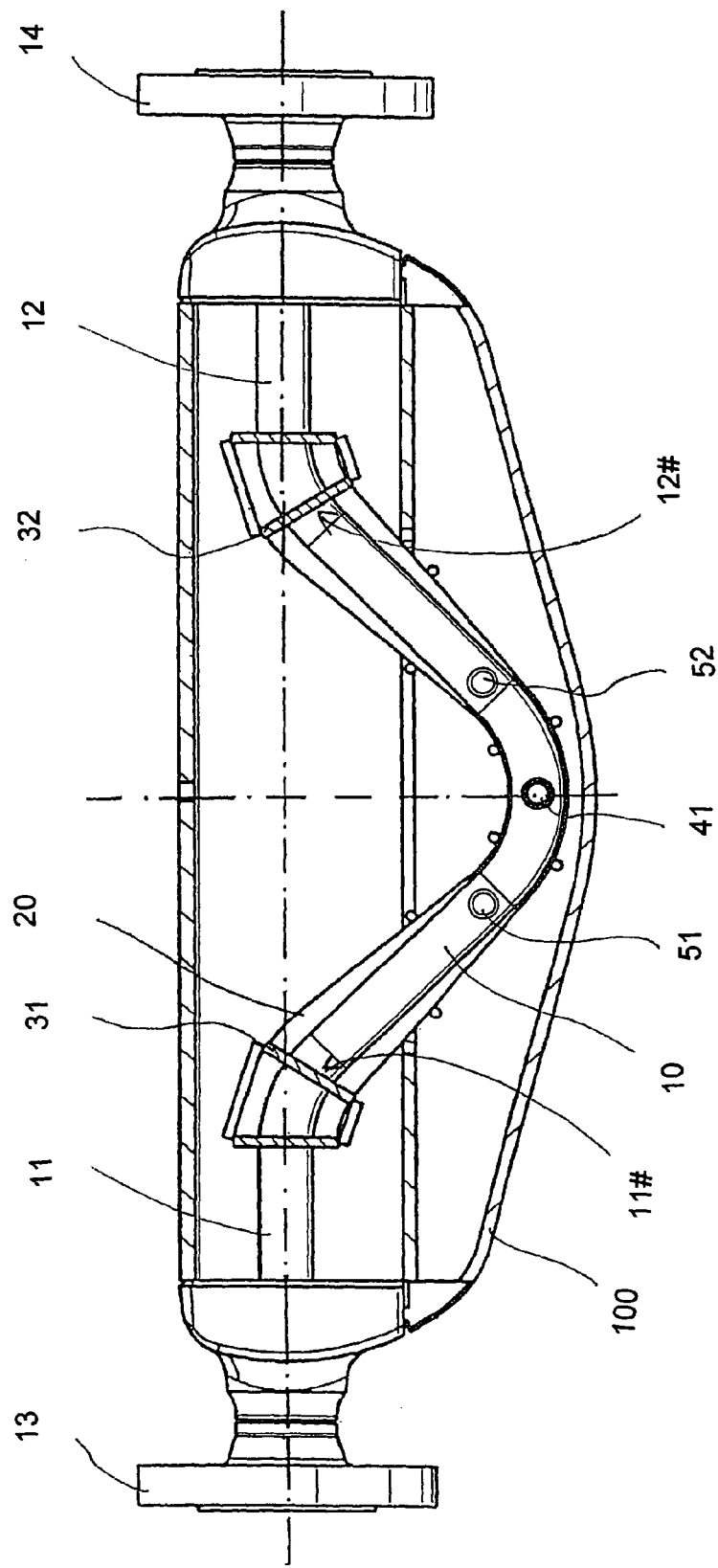

For conveying the flowing medium, the inner part of the measuring transducer generally comprises a first—in the example of an embodiment shown in FIGS. 4 and 5 a single— at least sectionally curved, measuring tube 10, which extends with an oscillatory length $L_{10}$ between an inlet-side, first measuring tube end 11# and an outlet-side, second measuring tube end 12#, and which, for the production of the aforementioned reaction forces, is caused during operation to vibrate at least over its oscillatory length $L_{10}$ and is thereby, oscillating about a static, rest position, repeatedly elastically deformed. The oscillatory length $L_{10}$ here corresponds to—as is again also schematically represented in FIG. 8—a length of an imagined central or centroidal axis in the form of an imaginary connecting line through the centers of gravity of all cross-sectional areas of the measuring tube extending within the lumen; in the case of a curved measuring tube, thus a laid out straight length of the measuring tube 10.

Figure 6:
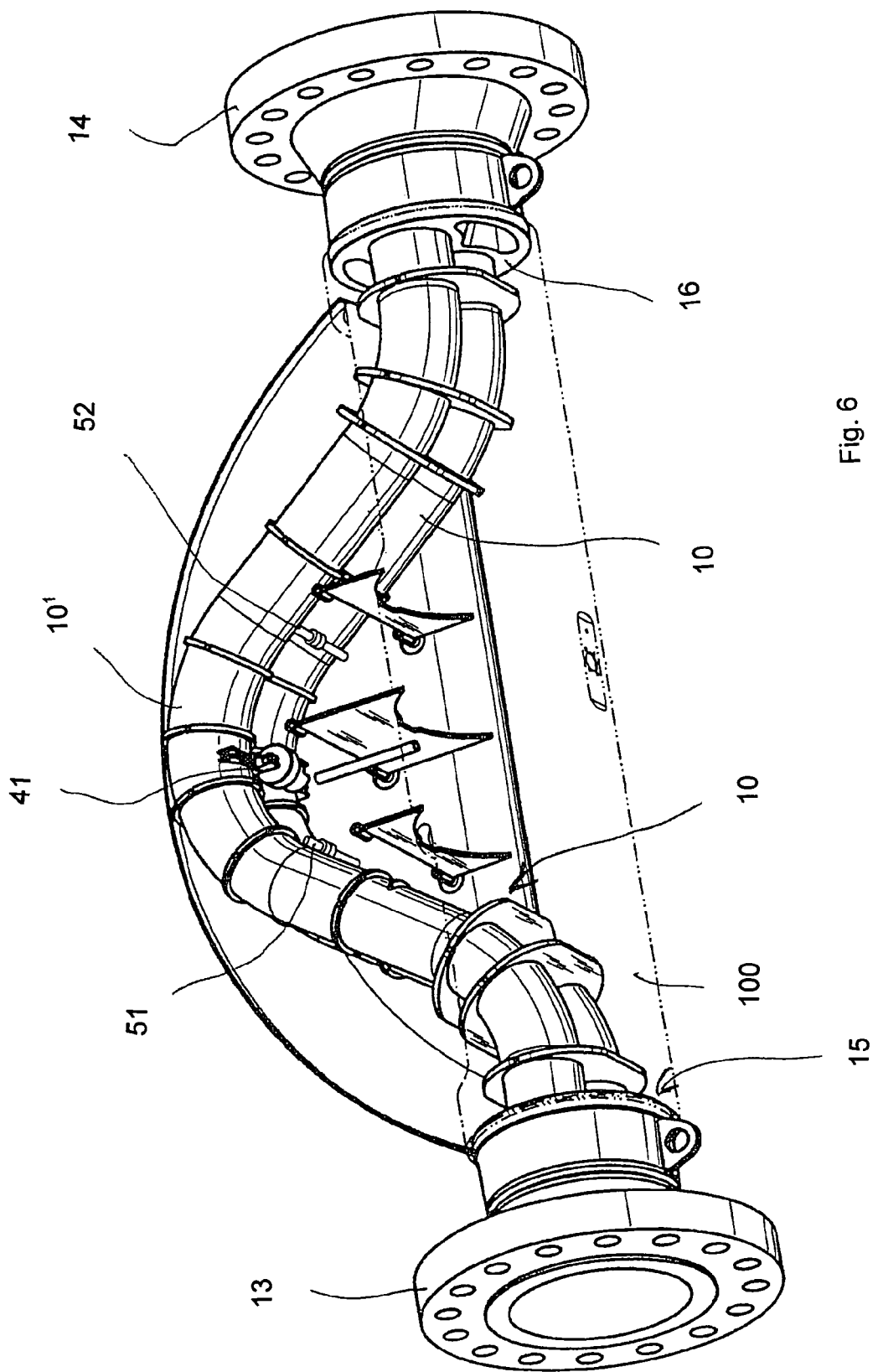
FIGS. 6, and 7 respectively, in partially sectioned and perspective views, a further variant of a vibration-type measuring transducer, particularly suited for a measuring system according to FIGS. 2a, 2b.
Figure 7:
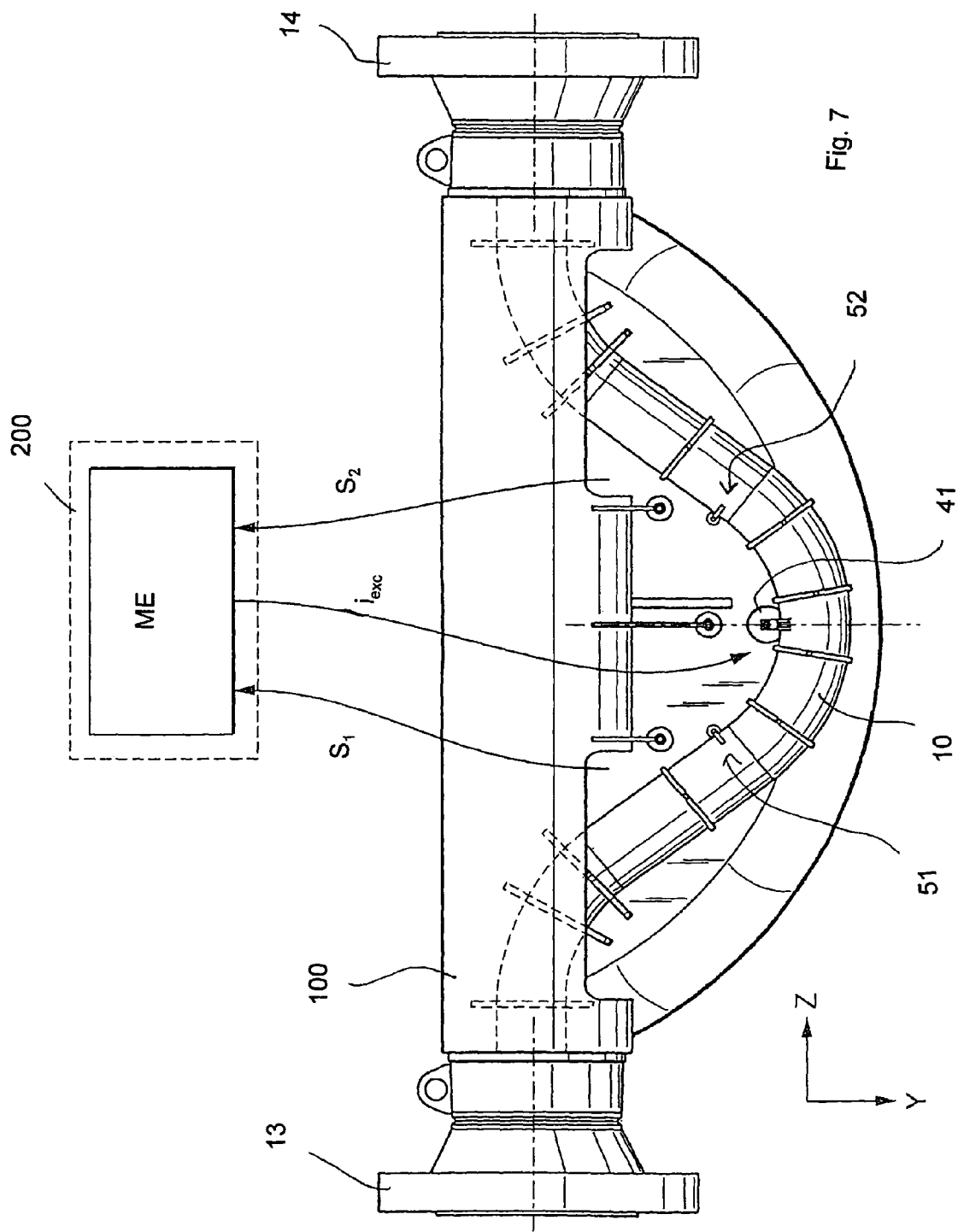

It should at this point be expressly pointed out that— although the measuring transducer in the example of an embodiment shown in FIGS. 4 and 5 solely exhibits a single measuring tube and, at least in this respect, resembles in its mechanical construction as well as its principle of action the measuring transducers proposed in U.S. Pat. No. 7,360,451 or U.S. Pat. No. 6,666,098, or those measuring transducers available for purchase under the type designation "PROMASS H", "PROMASS P" or "PROMASS S"—measuring transducers with greater than one measuring tube can of course also serve for the implementation of the invention, for example measuring transducers comparable to those illustrated in the previously mentioned U.S. Pat. No. 5,796,011, U.S. Pat. No. 5,731,527, or U.S. Pat. No. 6,920,798, or, for example, those measuring transducers made available on the market on the part of the assignee under the type designation "PROMASS E" or "PROMASS F", which in each case have two parallel measuring tubes. In accordance therewith, the measuring transducer can also exhibit two measuring tubes for conveying the medium to be measured, which are mechanically coupled with each other—for example by means of an inlet-side distributor element and an outlet-side distributor element, in given cases also additionally by means of at least one inlet-side coupling element and at least one outlet side coupling element—and/or which are equally embodied to each other and/or curved and/or parallel to each other; and which, during operation, for the production of the primary signal, at least at times vibrate, for instance at an equal, shared oscillation frequency, but with opposite phase to each other. According to a further development of the invention, the measuring transducer thus includes (for instance as schematically represented in FIGS. 6 and 7), in addition to the first measuring tube 10, a second measuring tube 10', which—with the forming of a first coupling zone on the inlet side by means of a (for example plate-shaped) first coupling element, and with the forming of a second coupling zone on the outlet side by means of a second (for example plate-shaped and/or of equal construction to the first coupling element) coupling element—is mechanically connected to the first measuring tube 10. In this case as well, the first coupling zone in each case defines a first measuring tube end 11#, 11'# on the inlet side of each of the two measuring tubes 10, 10'; and the second coupling zone in each case defines a second measuring tube end 12#, 12'# on the outlet side of each of the two measuring tubes 10, 10'. Since for the case in which the inner part is formed by means of two measuring tubes, each of the two measuring tubes 10, 10' (which, during operation, especially oscillate with opposite-phase to each other and/or are equally embodied as regards shape and material) serves to convey the measured medium, according to a further embodiment of these two variants of the measuring transducer according to the invention, each of the two measuring tubes in each case communicates on the inlet-side with a shared first distributor element 15 of the measuring transducer (which divides a medium flowing in into two flow portions), and in each case on the outlet side with a second shared distributor element 16 of the measuring transducer (which guides the flow portions back together), so that during operation of the measuring system, both measuring tubes are flowed through by the medium in a simultaneous and parallel fashion.

Figure 8:
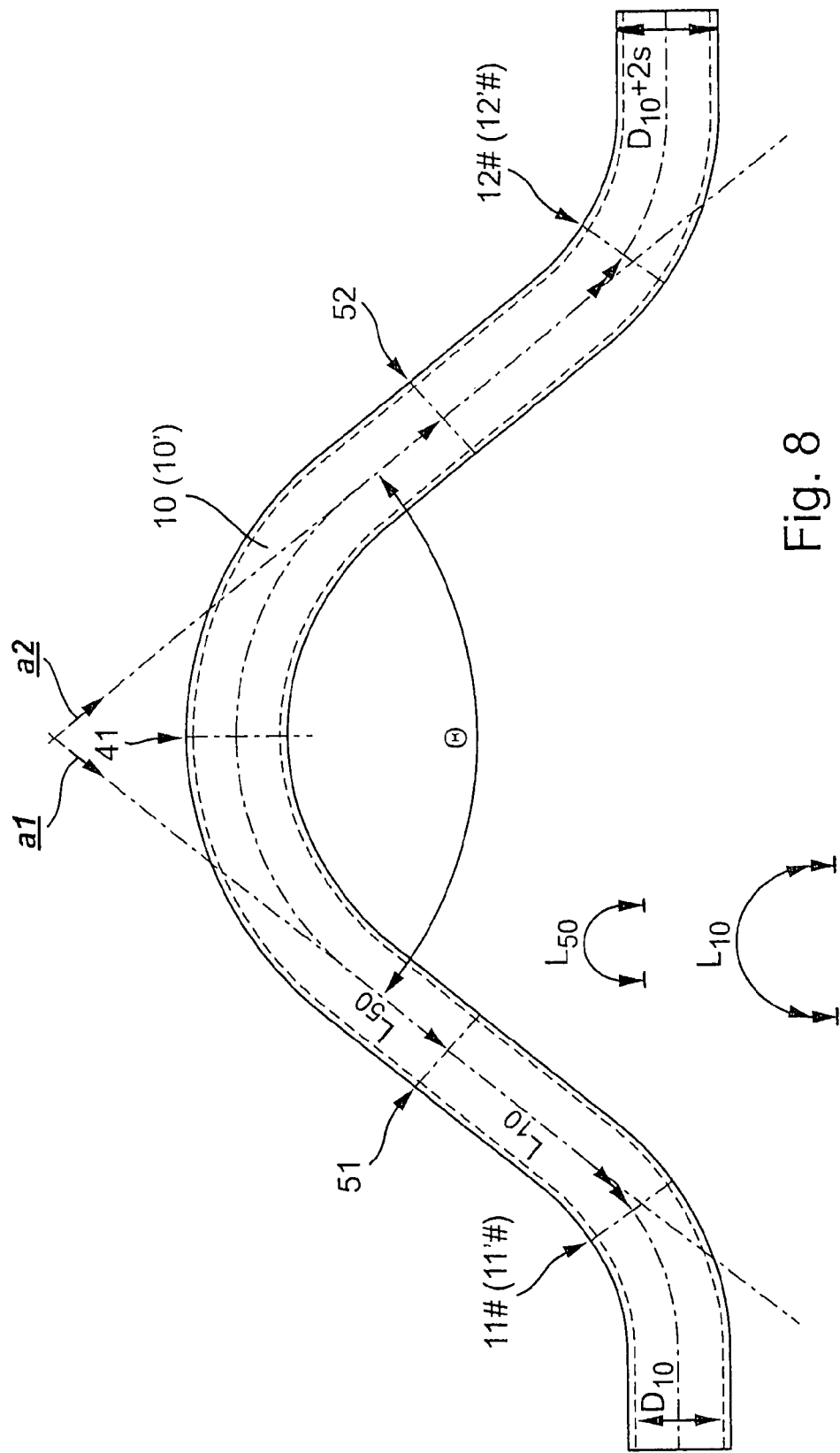
FIG. 8 schematically in side view, a measuring tube, particularly one suited for use in a measuring transducer according to FIGS. 4 and 5 or FIGS. 6 and 7.

As is directly evident from the combination of FIGS. 4 and 5, and, respectively, 6 and 7 as well as also FIG. 8, the at least one measuring tube 10 is—as is usual in the case of measuring tubes of the type discussed—in each case shaped in such a way, that the aforementioned central axis lies in an imaginary tube plane of the measuring transducer. According to one embodiment of the invention, in such a case, the at least one measuring tube 10 is caused during operation to vibrate in such a way, that it oscillates (especially in a bending oscillation mode) about an oscillation axis that is parallel to or coincides with the imagined connecting axis imaginarily connecting the two measuring tube ends 11#, 12#. The at least one measuring tube 10 is furthermore shaped and arranged in the measuring transducer in such a way, that the aforementioned connecting axis runs essentially parallel to, or, in given cases, also coincides with, an imagined longitudinal axis L of the measuring tube imaginarily connecting the inlet and outlet ends of the measuring transducer.

Since the measuring transducer should be usable for a large number of different applications (especially in the field of industrial measurements and automation technology), it is further provided that the at least one measuring tube exhibits a caliber $D_{10}$ (corresponding to tube inner diameter) which amounts to greater than 1 mm, especially greater than 5 mm. For the purpose of achieving an oscillatory amplitude (especially in bending oscillation mode) high enough for the desired accuracy of measurement, according to one embodiment of the invention, the at least one measuring tube further exhibits a wall thickness s, which amounts to less than 7 mm and especially less than 3 mm, especially in such a way that an areal moment of inertia $I_{10}$ of a cross-section of the measuring tube, which is defined by the relationship $$I_{10} = \frac{\pi}{64} \cdot [D_{10}^4 - (D_{10} + s)^4],$$

amounts to greater than 40 mm$^4$, and especially greater than 150 mm$^4$.

The at least one measuring tube 10 (which is, for example, made of stainless steel, titanium, tantalum, zirconium or an alloy of these) of the measuring transducer—and in this respect an imagined central axis of the measuring tube 10 extending within the lumen as well—can, for example, be embodied in an essentially U-shaped, or, as is also illustrated in FIGS. 4 and 5, FIGS. 6 and 7 or FIG. 8, in an essentially V-shaped manner.

In accordance therewith, according to a further embodiment of the invention, the at least one measuring tube exhibits 1) an inlet-side, first straight tube segment with an imaginary longitudinal axis that exhibits a direction vector a1 pointing toward the first coupling zone, and 2) an outlet-side, second straight tube segment with an imaginary longitudinal axis that exhibits a direction vector a2 pointing toward the second coupling zone. As is immediately evident from FIGS. 4 and 5 and, respectively, FIGS. 6 and 7, the two straight segments of tube are, as is quite usual in measuring tube geometry of this sort, connected with one another by means of an arc-shaped—here essentially circularly arc-shaped—tube segment. For the purpose of forming as compact a measuring transducer as possible with an overall as short as possible installed length, the arc-shaped tube segment is, according to a further embodiment of the invention, here further designed in such a way that, measured from its central axis, it exhibits an average tube arc radius R that amounts to less than 500 mm, especially less than 300 mm. The two straight segments of tube of the at least one measuring tube 10 are further arranged with respect to each other in such a way, that (as is schematically represented in FIG. 8) the direction vector a1 of the imagined longitudinal axis of the first straight tube segment and the direction vector a2 of the imagined longitudinal axis of the second straight tube segment intersect to form an angle Θ. The size of the angle Θ is, in the case where the two straight segments of tube are connected with each other via a circular arc-shaped tube segment, determined by the tube arc radius R as well as the corresponding arc length B of the arc-shaped tube segment, for instance using radians, by $$\Theta = \frac{B}{R},$$

and, using degrees, by $$\Theta = \frac{180°}{\pi} \cdot \frac{B}{R}.$$

In particular, the two straight segments of tube of the at least one measuring tube are arranged with respect to one another in such a way, that the angle $\Theta$ has a size of less than 160° and/or greater than 20°. Alternatively or in addition to this, according to another embodiment of the invention, the arc-shaped tube segment is designed in such a way, that a tube arc radius to tube outer radius ratio R' (defined by ratio of the tube arc radius R to a tube outer radius corresponding to the measuring tube caliber $D_{10}$ and the wall thickness s, $r=0.5 \cdot D_{10}+s$, of the arc-shaped tube segment) amounts to less than 60 (especially less than 50) and/or greater than 3 (especially greater than 4).

For minimizing disturbing influences affecting the inner part formed by means of a single measuring tube, as well as for reducing oscillatory energy released on the part of the respective measuring transducer upon the connected process line as a whole, according to the example of an embodiment shown in FIGS. 4 and 5, the inner part of the measuring transducer moreover includes a counteroscillator 20 (for example embodied in a U or V shape), which is mechanically coupled with the—here single—measuring tube. The counteroscillator 20 is (as is also shown in FIG. 2) arranged in the measuring transducer spaced laterally to the measuring tube 10, and—forming on the inlet side a first coupling zone (ultimately defining the aforementioned first measuring tube end 11#), and forming on the outlet side a second coupling zone (ultimately defining the aforementioned second measuring tube end 12#)—is, at each location, affixed to the measuring tube 10. The counteroscillator 20—here running essentially parallel to the measuring tube 10, in given cases also arranged coaxially to this—is manufactured from a metal compatible with the measuring tube as regards thermal expansion behavior, for example steel, titanium or zirconium, and can in such a case also be embodied, for example, in a tube-shaped or essentially box-shaped fashion. As is shown in FIG. 2, or, among other things, proposed in U.S. Pat. No. 7,360,451, the counteroscillator 20 can be formed for example by means of plates arranged to the left and right sides of the measuring tube 10, or by means of blind tubes arranged to the left and right sides of the measuring tube 10. Alternatively, the counteroscillator 20 can be formed by means of a single blind tube running laterally and parallel to the measuring tube, as is, for instance, proposed in U.S. Pat. No. 6,666,098. As is evident from a comparison of FIGS. 2 and 3, in the example of an embodiment shown here, the counteroscillator 20 is held on the inlet side by means of at least a first coupler 31 on the first measuring tube end 11#, and on the outlet side by means of at least a second coupler 32 (especially one essentially identical to the first coupler 31) on the second measuring tube end 12#. For the couplers 31, 32, simple node plates, for example, can be used here, which in each case are secured on the outlet and inlet sides to the measuring tube 10 and the counteroscillator 20 in a corresponding manner. Furthermore—as is shown in the example of an embodiment illustrated in FIGS. 2 and 3—a completely closed box (or, in given cases, a box with a partially open frame), formed by means of node plates spaced apart from each other in the direction of the imaginary longitudinal axis L of the measuring transducer together with protruding ends of the counteroscillator 20 on the outlet and inlet sides, respectively, can also serve as a coupler 31 or as a coupler 32. As is schematically represented in FIGS. 1 and 2, the measuring tube 10 is furthermore connected via a straight first connecting tube piece 11—which opens on the inlet side in the area of the first coupling zone—and a straight second connecting tube piece 13 (especially one essentially identical to the first connecting tube piece 11)—which opens on the outlet side in the area of the second coupling zone—to the process line (not shown here) responsible for conveying the medium to and away from the system; wherein an inlet end of the inlet-side connecting tube piece 11 practically forms the inlet end of the measuring transducer, and an outlet end of the outlet-side connecting tube piece 12 practically forms the outlet side of the measuring transducer. Advantageously, the measuring tube 10, together with the two connecting tube piece 11, 12, can be realized in a one-piece fashion, so that, for example, a single tubular stock or semifinished part, made of a material typical for such measuring transducers (such as stainless steel, titanium, zirconium, tantalum or a corresponding alloy of this), can be used for their production. Instead of the measuring tube 10, the inlet tube piece 11 and the outlet tube piece 12 in each case being formed from segments of a single, one-piece tube, these parts can, if required, also be produced by means of a single, subsequently joined together (e.g. welded together) stock or semifinished part. It is further provided in the example of an embodiment shown in FIGS. 2 and 3 that the two connecting tube pieces 11, 12 are arranged in such a way with respect to both each other and an imagined longitudinal axis L of the measuring transducer which imaginarily connects the two coupling zones 11#, 12#, that the inner part formed here by means of the counteroscillator and measuring tube can move in a pendulum like fashion about the longitudinal axis L, accompanied by twistings of the two connecting tube pieces 11, 12. For this reason, the two connecting tube pieces 11, 12 are arranged in such a way with to respect to each other that the essentially straight segments of tube run essentially parallel to the imagined longitudinal axis L or the imagined oscillation axis of the bending oscillations of the measuring tube, and the segments of tube essentially align both with the longitudinal axis L as well as with each other. Since the two connecting tube pieces 11, 12 in the here illustrated example of an embodiment are embodied to be essentially straight practically over their entire length, they are correspondingly, on the whole, oriented essentialy in alignment with one another as well as with the imaginary longitudinal axis L. As is additionally evident from FIGS. 2 and 3, the transducer housing 100—which especially is bend and torsion-resistant in comparison with the measuring tube 10—is affixed—especially rigidly—to an inlet end of the inlet-side connecting tube piece 11 which is distal with regard to the first coupling zone, as well as to an outlet end of the outlet-side connecting tube piece 12 which is distal with regard to the second coupling zone. In this respect, the entire inner part—here formed by means of the measuring tube 10 and counteroscillator 20—is not only completely encased by the transducer housing 100, but also, as a result of its own particular mass and the spring effect of the two connecting tube pieces 11, 12, is held in the transducer housing 100 in an oscillatable manner.

For the case in which the measuring transducer MT is mounted in the process line (for example embodied as a metal pipeline) in a releasable manner, a first connecting flange 13 is provided on the inlet side of the measuring transducer and a second connecting flange 14 on the outlet side. In such a case, the connecting flanges 13, 14 can—as is quite usual in the case of measuring transducers of the type described—also be integrated at least partially terminally into the transducer housing 100. If required, the connecting tube pieces 11, 12 can, however, also be connected directly with the process line, e.g. by means of welding or hard soldering. In the example of an embodiment shown in FIGS. 2 and 3, the first connecting flange 13 is integrally molded on the inlet end of the inlet-side, connecting tube piece 11, and the second connecting flange 14 is integrally molded on the outlet end of the outlet-side, connecting tube piece 12; whereas in the example of an embodiment shown in FIGS. 4 and 5, the connecting flange is correspondingly connected with the associated distributor elements.

For actively exciting mechanical oscillations of the at least of measuring tube (or measuring tubes) 10, each of the measuring transducers shown in FIGS. 4 through 7 includes an exciter mechanism 40, especially an electrodynamic exciter mechanism. This—driven by a correspondingly conditioned exciter signal (e.g. with a controlled electrical current and/or a controlled voltage) delivered by a driver circuit of the measuring device electronics and, in given cases, interacting with the evaluating circuit—serves in each case to convert electrical exciter energy $E_{exc}$, fed in by means of the driver circuit, into an exciter force $F_{exc}$, which acts upon the at least one measuring tube 10 (for example harmonically or with a pulse shape), and which deflects the measuring tube 10 in the manner described above. The exciter force $F_{exc}$, can, as is typical in the case of measuring transducers of this sort, be developed bidirectionally or unidirectionally, and, in the manner known in the art (e.g. by means of a current and/or voltage control circuit), can be adjusted with regard to its amplitude, and (for example by means of a phase control loop) with regard to its frequency. The exciter mechanism 40 can be, for example, a mechanism formed in conventional manner by means of a—for example single—electrodynamic oscillation exciter 41, which acts centrally (that is to say in the region of half of the oscillation length $L_{10}$) on the respective measuring tube, can be used. The oscillation exciter 41 can, in the case of an inner part formed by means of a counteroscillator and measuring tube, as indicated in FIG. 4) be formed, for example, by means of a cylindrical exciter coil attached to the counteroscillator 20—for example a coil through which, during operation, a corresponding electrical exciter current flows, and which, in association therewith, is permeated by a corresponding magnetic field—as well as by means of a permanently magnetic armature, which is affixed externally (especially centrally) to the measuring tube 10, and which at least partially plunges into the exciter coil. Additional exciter mechanisms for oscillations of the at last one measuring tube which are also quite suitable for the measuring system of the invention are illustrated, for example, in the previously mentioned U.S. Pat. No. 5,705,754, U.S. Pat. No. 5,531,126, U.S. Pat. No. 6,223,605, U.S. Pat. No. 6,666,098 or U.S. Pat. No. 7,360,451.

According to a further embodiment of the invention, during operation, the at least one measuring tube 10 is, by means of the exciter mechanism, at least at times actively excited in a wanted mode, in which it performs (especially predominantly or exclusively) bending oscillations about the aforementioned imagined oscillation axis, for example predominantly with exactly one resonance frequency of the respective measuring transducer (or of the inner part of the measuring transducer which forming such) for example, that resonance frequency which corresponds to a fundamental bending oscillation mode, in which the at least one measuring tube exhibits exactly one oscillatory antinode. It is particularly provided here that the at least one measuring tube 10—as is quite typical by measuring transducers of this sort with curved measuring tubes—is excited by means of the exciter mechanism to bending oscillations at an excitation frequency $f_{exc}$, and in such a way that, in the wanted mode, the measuring tube 10, oscillating (for example in the manner of a cantilever clamped on one end) about the oscillation axis mentioned, bends at least partially outwards according to one of its natural bending oscillation forms. In such a case, the bending oscillations of the measuring tube exhibit, in the region of the inlet-side coupling zone (which defines the inlet-side, measuring tube end 11#), an inlet-side oscillation node; and, in the region of the outlet-side coupling zone (which defines the outlet-side, measuring tube end 12#), an outlet-side oscillation node, so that the measuring tube extends, essentially freely oscillating, with an oscillatory length $L_{10}$ between these two oscillation nodes. If required, the vibrating measuring tube can also—as for example proposed in U.S. Pat. No. 7,077,014 or JP-A 9-015015—be targetedly influenced in its oscillatory movements by means of spring-elastic or electromotive coupling elements which correspondingly further act on the measuring tube in the region of the oscillatory length. The driver circuit can, for example, be embodied as a phase control loop (PLL), which is used in the manner known in the art to continually adjust an exciter frequency $f_{exc}$ of the exciter signal to the instantaneous eigenfrequency of the desired wanted mode. The construction and the application of such phase control loops for the active excitation of measuring tubes to oscillations at a particular mechanical frequency is, for example, described in detail in U.S. Pat. No. 4,801,897. Other driver circuits known per se in the art can and suitable for adjusting the exciter energy $E_{exc}$ can of course also be used, such as, for example, according to the previously mentioned state of the art, for instance, the previously mentioned U.S. Pat. No. 4,777,833, U.S. Pat. No. 4,801,897, U.S. Pat. No. 4,879,911, U.S. Pat. No. 5,009,109, U.S. Pat. No. 5,024,104, U.S. Pat. No. 5,050,439, U.S. Pat. No. 5,804,741, U.S. Pat. No. 5,869,770, U.S. Pat. No. 6,073, 495 or U.S. Pat. No. 6,311,136. With regard to a use of such driver circuits for vibration-type measuring transducers, reference should furthermore be made to the measuring device electronics provided with measurement transmitters of the series, "PROMASS 83". Such measuring device electronics are offered by the assignee, for example, in connection with measuring transducers of the series "PROMASS E", "PROMASS F", "PROMASS H", "PROMASS I", "PROMASS P" or "PROMASS S". The driver circuits of these are, for example, embodied in such a way that the lateral bending oscillations in the wanted mode are regulated to a constant amplitude, thus an amplitude largely independent of density $\rho$.

For causing vibrations of the at least one measuring tube 10, the exciter mechanism 40, is, as previously mentioned, fed by means of a likewise oscillating, exciter signal of adjustable frequency $f_{exc}$, so that during operation, the exciter coil of the oscillation exciter (here a single exemplar acting on the measuring tube 10) is flowed through by an electrical excitation current $i_{exc}$ correspondingly controlled with regard to its amplitude), whereby the magnetic field required for moving the measuring tube is produced. The driver or exciter signal (or the excitation current $i_{exc}$ thereof) can be, for example, harmonic, multifrequent or rectangular. In the case of the measuring transducer shown in the example of an embodiment, the exciter frequency $f_{exc}$ of the electrical excitation current $i_{exc}$ necessary for maintaining the bending oscillation of the at least one measuring tube 10 can, advantageously, be chosen and adjusted in such a way that the laterally oscillating measuring tube 10 at least predominantly oscillates in a bending oscillation mode with a single oscillatory antinode. In accordance therewith, according to an additional embodiment of the invention, the exciter or wanted mode frequency $f_{exc}$ is adjusted in such a way, that it corresponds as precisely as possible to an eigenfrequency of bending oscillations of the measuring tube 10, especially that of the fundamental bending oscillation mode. In the case of the use of a measuring tube made of stainless steel (especially Hastelloy) with a caliber $D_{10}$ of 29 mm, a wall thickness s of about 1.5 mm, an oscillatory length of about 420 mm and a chordal length (measured between the two ends of the measuring tube) of 305 mm, the resonance frequency corresponding to the fundamental bending oscillation mode of the same—for example in the case of a density of practically zero (e.g. in the case of a measuring tube filled solely with air)—would amount to about 490 Hz.

In the example of an embodiment shown in FIGS. 4 and 5, with an inner part formed by means of a measuring tube and counteroscillator, the measuring tube 10 performs bending oscillations (which are actively excited by means of the exciter mechanism) predominantly relative to the counteroscillator 20, especially at a common frequency and with mutually opposite phase. In the case of an exciter mechanism simultaneously (for example differentially) acting on both the measuring tube and the counteroscillator, the counteroscillator 20 is in such a case also forcibly excited to simultaneous cantilever oscillations, and indeed in such a way that it oscillates at an equal frequency—however, at least partially out of phase, and especially essentially opposite phase—to the measuring tube 10 oscillating in the wanted mode. In particular, the measuring tube 10 and the counteroscillator 20 are, in such a case, furthermore matched to each other in such a way—and especially excited in such a way—that during operation, they at least at times and at least partially perform opposite-equal—that is equal frequency, but essentially opposite phase—bending oscillations about the longitudinal axis L. The bending oscillations can, in such a case, be formed in such a way that they are of equal modal order and, at least in the case of a resting fluid, also essentially of an equal shape; otherwise, in the case of the use of two measuring tubes, the measuring tubes—as is typical in the case of measuring transducers of the type being discussed—are, by means of the exciter mechanism (especially an exciter mechanism acting differentially between the two measuring tubes 10, 10'), actively excited in such a way that during operation, they at least at times perform opposite-equal bending oscillations about the longitudinal axis L. In other words, the two measuring tubes 10, 10' and the counteroscillator 20 in each case move in the manner of tuning fork tines oscillating relative to one another.

In the case operationally provided, in which the medium flows through the process line and thus the mass flow m is different from zero, by means of the measuring tube 10 vibrating in the manner described above, Coriolis forces are induced in the medium flowing through. These in turn react upon the measuring tube 10, and thereby cause an additional deformation of the same (which can be registered by sensors), in essence according to a further particular oscillation form of a higher modal order than the wanted mode. An instantaneous value of this so-called Coriolis mode (which is of equal frequency to, and superimposed on, the wanted mode) is in such a case (especially with regard to its amplitude) also dependant on the instantaneous mass flow m. For the Coriolis mode—as is typical in the case of measuring transducers of this sort with curved measuring tubes—can be used, for example, the particular oscillation form of the anti-symmetrical twist mode, that is to say that particular oscillation mode, in the case of which the measuring tube 10 (as already mentioned) also performs rotary oscillations about an imagined rotary oscillation axis which is perpendicular to the bending oscillation axis and which imaginarily intersects the central axis of the measuring tube 10 in the region of half the oscillation length $L_{10}$.

For registering oscillations (especially bending oscillations) of the at least one measuring tube 10, especially those oscillations in Coriolis mode, the measuring transducer further exhibits a corresponding sensor arrangement 50. This comprises—as is also schematically represented in FIGS. 4 through 7—a first oscillation sensor 51 (especially an electrodynamic oscillation sensor)—which is arranged on the at least one measuring tube spaced apart from the at least one oscillation exciter, and which delivers a first primary signal $s_1$ (for example a voltage corresponding to the oscilations or a current corresponding to the oscillations) of the measuring transducer representing a vibration of the measuring tube 10—as well as a second oscillation sensor 52 (especially an electrodynamic oscillation sensor), which is arranged on the at least one measuring tube spaced apart from the first oscillation sensor 51, and which delivers a second primary signal $s_2$ of the measuring transducer representing a vibration of the measuring tube 10. A length of the region of the associated measuring tube (especially a region vibrating in an essentially freely oscillating manner) extending between the two (for example equally embodied) oscillation sensors here corresponds to a measuring length $L_{50}$ of the respective measuring transducer (as is again also schematically represented in FIG. 8). In such a case, each of the (typically broadband) primary signals $s_1$, $s_2$ of the measuring transducer MT exhibits a signal component corresponding to the wanted mode, and having 1) a signal frequency corresponding to the instantaneous oscillation frequency, $f_{exc}$, of the at least one measuring tube 10 oscillating in the actively excited, wanted mode and 2) a phase shift (dependent on the current mass flow of the medium flowing in the at least one measuring tube 10) relative to the exciter signal $i_{exc}$ generated, for example, by means of PLL as a function of a phase difference existing between at least one of the oscillatory measurement signals $s_1$, $s_2$ and the exciter current in the exciter mechanism. Even in the case of the use of a rather broadband exciter signal $i_{exc}$, as a result of the usually very high oscillation quality factor of the measuring transducer MT, it can be assumed that the signal component of each of the primary signals which corresponds to the wanted mode outweighs other signal components—especially those corresponding with possible external disturbances and/or those to be classified as noise—and in this respect that this component is dominating, at least within a frequency range corresponding to a bandwidth of the wanted mode.

In the examples of embodiments shown here, the two oscillation sensors are in each case arranged on the at least one measuring tube 10, with first oscillation sensor 51 on the inlet side, and the second oscillation sensor 52 on the outlet side; and especially with the second oscillation sensor spaced as equally far from the at least one oscillation exciter (or the halfway point of the measuring tube 10) as the first oscillation sensor is. As is quite typical in the case of vibration-type measuring transducers of this type which are used in a measuring system embodied as a Coriolis mass flow measuring device, the first oscillation sensor 51 and the second oscillation sensor 52 are, according to one embodiment of the invention, in each case furthermore arranged in the measuring transducer on a side of the measuring tube occupied by the oscillation exciter 41. Moreover, the second oscillation sensor 52 can also be arranged in the measuring transducer on the side of the measuring tube occupied by the first oscillation sensor 51. The oscillation sensors of the sensor arrangement can furthermore advantageously be embodied in such a way that they deliver primary signals of an equal type, for example in each case as a signal voltage or electrical signal current. According to an additional embodiment of the invention, both the first oscillation sensor and the second oscillation sensor are in each case furthermore placed in the measuring transducer MT in such a way, that each of the oscillation sensors at least predominantly registers vibrations of the at least one measuring tube 10. For the case described above, in which the inner part is formed by means of a measuring tube and a counteroscillator coupled thereto, according to a further embodiment of the invention, both the first oscillation sensor and the second oscillation sensor are embodied and placed in the measuring transducer in such a way, that each of the oscillation sensors predominantly (and especially differentially) registers oscillations of the measuring tube relative to the counteroscillator; and in such a way that both the first primary signal $s_1$ and the second primary signal $s_2$ represent (especially opposite-equal) oscillatory movements of the at least one measuring tube 10 relative to the counteroscillator 20.

For the other case described, in which the inner part is formed by means of two measuring tubes (especially which during operation oscillate opposite-equal to each other), according to another embodiment of the invention, both the first oscillation sensor and the second oscillation sensor are embodied and placed in the measuring transducer in such a way, that each of the oscillation sensors predominantly (and especially differentially) registers oscillations of the first measuring tube 10 relative to the second measuring tube 10'; and in such a way that both the first primary signal $s_1$ and the second primary signal $s_2$ represent (especially opposite-equal) oscillatory movements of the two measuring tubes relative to one another. According to an additional embodiment of the invention, it is provided that the sensor mechanism exhibits exactly two oscillation sensors—that is to say no further oscillation sensors in addition to the first and second oscillation sensors—and in this respect corresponds to a conventional sensor arrangement as regards the components used.

The oscillation measurement signals $s_1$, $s_2$ delivered by the sensor arrangement—which in each case exhibit a signal component with a signal frequency corresponding to the instantaneous oscillation frequency $f_{exc}$ of the measuring tube oscillating in the actively excited, wanted mode—are, as is also shown in FIG. 3, fed to the measuring device electronics ME, and, in turn, to the measurement and evaluating circuit μC provided therein, where, by means of a corresponding input circuit FE, the signals are first preprocessed (especially preamplified, filtered and digitized) in order to subsequently be evaluated in a suitable fashion. For the input circuit FE, as well as the measuring and evaluating circuit μC, circuit technologies already used and established in traditional Coriolis mass flow measuring devices for the purpose of converting the primary signals or for ascertaining mass flow rates and/or totaled mass flows etc. can be used, especially those according to the previously mentioned state of the art. According to an additional embodiment of the invention, the measuring and evaluating circuit μC is accordingly realized by means of a microcomputer—for example realized by means of a digital signal processor (DSP)—provided in the measuring electronics ME, and by means of program code correspondingly implemented in and running on this microcomputer. The program code can, for example, be persistently stored in a non-volatile memory EEPROM of the microcomputer, and during the startup of the latter, can be loaded to a volatile memory RAM, e.g. one integrated into the microcomputer. Processors suitable for applications of this sort (e.g. those of the type TMS320VC33) are available from the firm Texas Instruments Inc. It is obvious in such a case that the primary signals $s_1$, $s_2$—as already suggested—are, for processing in the microcomputer, to be converted into corresponding digital signals by means of a corresponding analog-to-digital converter A/D of the measuring device electronics ME; compare this with the previously mentioned U.S. Pat. No. 6,311,136 or U.S. Pat. No. 6,073,495 or the aforementioned measurement transmitters of the series "PROMASS 83".

According to one embodiment of the invention', by means of the two primary signals $s_1$, $s_2$ delivered by the sensor arrangement 50—for example on the basis of a phase difference detected between the primary signals $s_1$, $s_2$, which are generated in the case of a measuring tube oscillating partially in the wanted and Coriolis modes—the measuring and evaluating circuit μC serves to recurringly ascertain a mass flow measured value $X_m$, which represents as accurately as possible the mass flow rate m to be measured for the medium conveyed through the measuring transducer. Alternatively or in addition to this, the measuring and evaluating circuit serves to ascertain—for example derived from a current mass flow value $X_m$ and/or from a large number of earlier sequentially produced and/or mass flow-measured values—a mass measured value $X_M$, which represents the instantaneous totaled mass flow, M. For this purpose, according to an additional embodiment of the invention, during operation, the evaluating circuit recurringly produces a phase difference value $X_{\Delta\phi}$, which represents the phase difference $\Delta\phi_I$ existing at the moment between the first primary signal $s_1$ and the second primary signal $s_2$. Furthermore, the evaluating circuit of the measuring system according to the invention can also, in the manner known in the art, serve to additionally generate a (for example digital) density measured value $X_\rho$, which represents an instantaneous density ρ of the medium to be measured; derived—for example on the basis of at least one of the primary signals delivered by the sensor arrangement—from an oscillation frequency of lateral bending oscillations (for example, those in the wanted mode) of the at least one measuring tube 10. Alternatively or in addition to this—as is quite typical in the case of in-line measuring devices of the type discussed—the evaluation unit can ascertain, or in given cases can also be used to ascertain, a (for example digital) viscosity measured value $X_\eta$, which represents an instantaneous viscosity of the medium, derived from the driver signal $i_{exc}$, which, as is known, can also serve as a measure for an apparent viscosity or a viscosity-density product of the medium conveyed by the measuring tube; compare, in this respect, U.S. Pat. No. 7,017,424, U.S. Pat. No. 6,840,109 or U.S. Pat. No. 6,651,513. In addition, it can readily be assumed that the measured values ascertained by the measuring device electronics (especially possible provisional values) are at least temporarily cached in the measuring device electronics ME (for example in the EEPROM-memory mentioned and/or in the RAM memory) and thus are held sufficiently long for subsequent uses. The aforementioned computational functions (especially those serving for the production of the mass flow measured value $X_m$ or for the production of each of the other respective measured values) can be implemented quite easily, for example by means of the above mentioned microcomputer of the evaluating circuit μC or by a digital signal processor DSP correspondingly provided therein. The creation and implementation of corresponding algorithms—which correspond to the previously described formulas or, also, for example, simulate the operation of the aforementioned amplitude or frequency control circuit for the exciter mechanism—as well as their translation in the measuring device electronics into correspondingly executable program codes is familiar in the art and therefore does not require—in any case not with respect to the present invention—a detailed explanation. The aforementioned formulas or other functionalities of the measuring system implemented by the measuring device electronics can, of course, readily be completely or partially implemented by means of a corresponding discretely embodied and/or hybrid (that is mixed analog-digital) computational circuit in the measuring device electronics.

Figure 9:
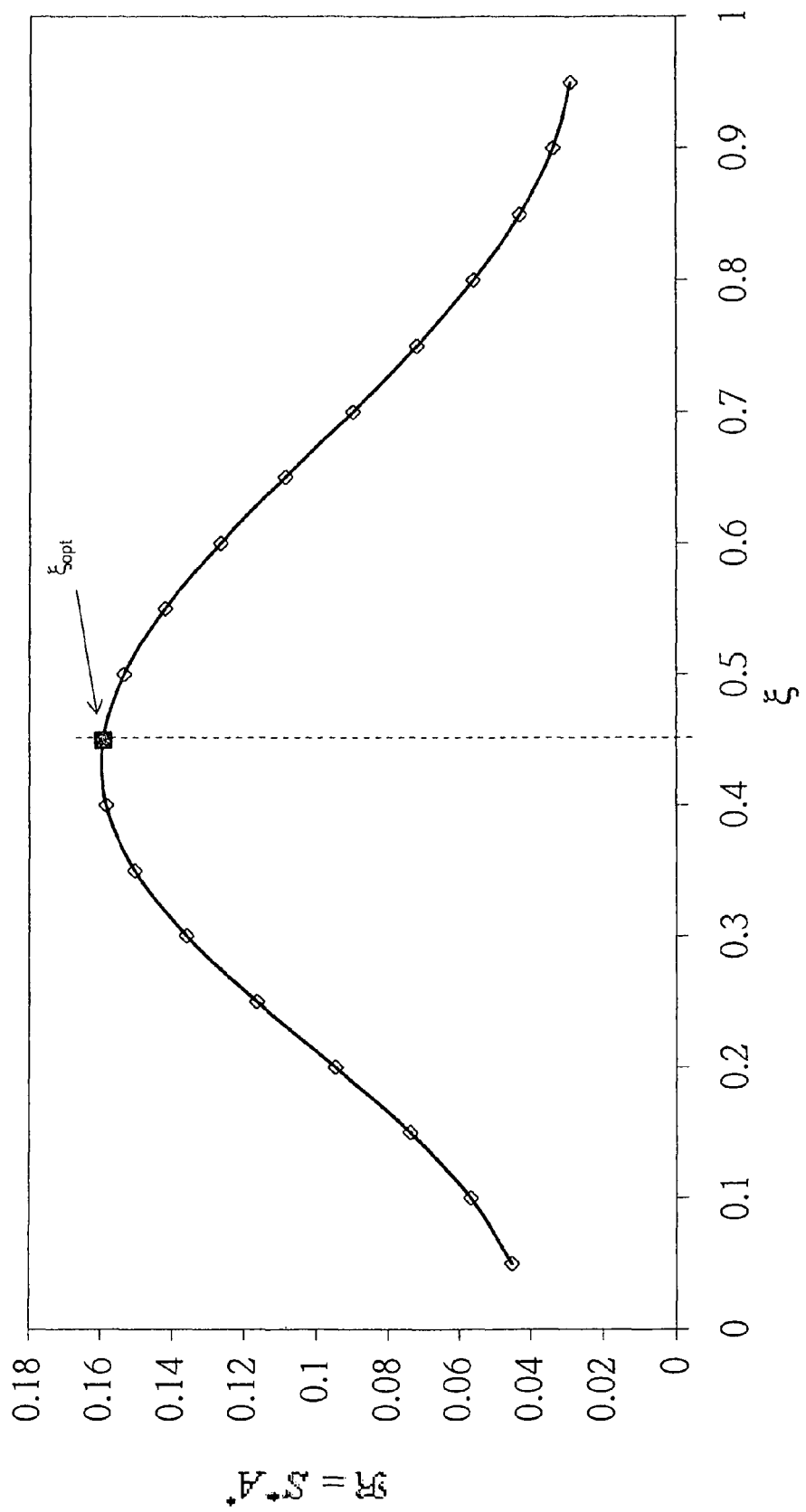
FIGS. 9 to 17 results of experimental investigations performed in connection with the invention, particularly with the use of computer-based simulation programs.

For achieving as high an efficiency as possible, with which the exciter power or exciter energy $E_{exc}$ (fed into the exciter mechanism during operation) is converted ultimately into the primary signals $s_1$, $s_2$ or into the signal variable (for instance, a signal amplitude, a signal frequency and/or a phase angle or a phase difference between the two primary signals, etc.) corresponding to the measured variable (e.g. the mass flow rate and/or the density) to in each case be registered by means of the measuring transducer—especially in such a way that the aforementioned condition $$\Re = \frac{A_{ACT}}{A_{MAX}} \cdot \frac{S_{ACT}}{S_{MAX}} = A^* S^*,$$

which virtually defines a universal optimizing function for measuring transducers of the type discussed, is as maximum as possible—the first oscillation sensor of the sensor arrangement and the second oscillation sensor of the sensor arrangement are, in the case of the measuring system according to the invention, placed in the measuring transducer in such a way that the measuring length $L_{50}$ of the measuring transducer corresponds to less than 65% (especially less than 55%) of the oscillatory length $L_{10}$, and greater than 25% (especially greater than 30%) of the oscillatory length $L_{10}$ (compare, in this connection, FIG. 9, especially in combination with FIG. 8). In other words, the two oscillation sensors are positioned optimally in the measuring transducer, when 1) the sensitivity $S_{ACT}$ actually achieved in the measuring transducer relative to the (theoretical) maximum possible sensitivity $S_{MAX}$—thus that particular sensitivity at a maximum measuring length corresponding to the oscillatory length $L_{10}$ ($L_{50}=L_{10}$)—and 2) the signal amplitude $A_{ACT}$ actually achieved during operation for the primary signals $s_1$, $s_2$ at the site of the oscillation sensors relative to the (theoretical) maximum possible oscillation amplitude $A_{ACT}$ at the site of the maximum oscillation amplitude—here at the oscillation exciter or at the point of half the oscillatory length $L_{10}$ ($L_{50}=0$)—are the maximum possible or approach the maximum possible; which, in turn, in the case of the usual measuring tube geometries, is, surprisingly enough, the aforementioned region between 65% and 30% of the oscillatory length $L_{10}$, a region hitherto not used for the positioning of the sensors (compare, in this connection, also FIG. 9).

Further investigations—especially by means of computer-based simulation calculations—on measuring transducers with typical measuring tube configurations—for example for curved measuring tubes with a caliber $D_{10}$ in the range between 10 mm and 250 mm—have in such case further shown that (as is for example readily evident from a combination of FIGS. 10, 11, 12, 14 14, 16 and 17) the first oscillation sensor of the sensor arrangement and the second oscillation sensor of the sensor arrangement are to be placed in the measuring transducer in such a way that, to the greatest degree possible, in the case of a measuring-length to oscillatory-length ratio $\xi=L_{50}/L_{10}$ (defined by a ratio of the measuring length $L_{50}$ to the oscillatory length $L_{10}$) the condition $\xi \leq 0.6$ is fulfilled, especially in such a way that the condition $\xi > 0.35$ is also fulfilled.

Figure 10:
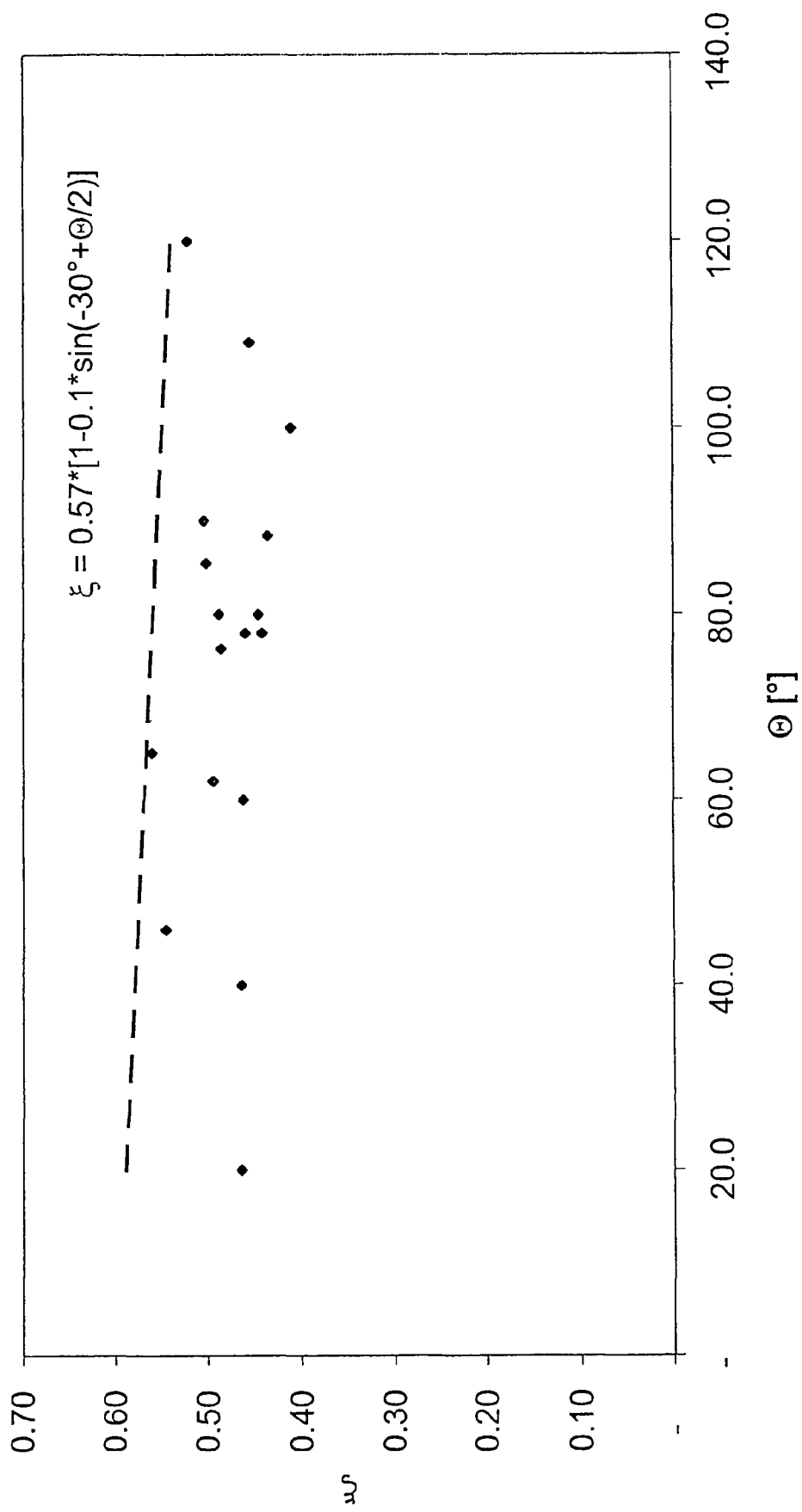
Figure 11:
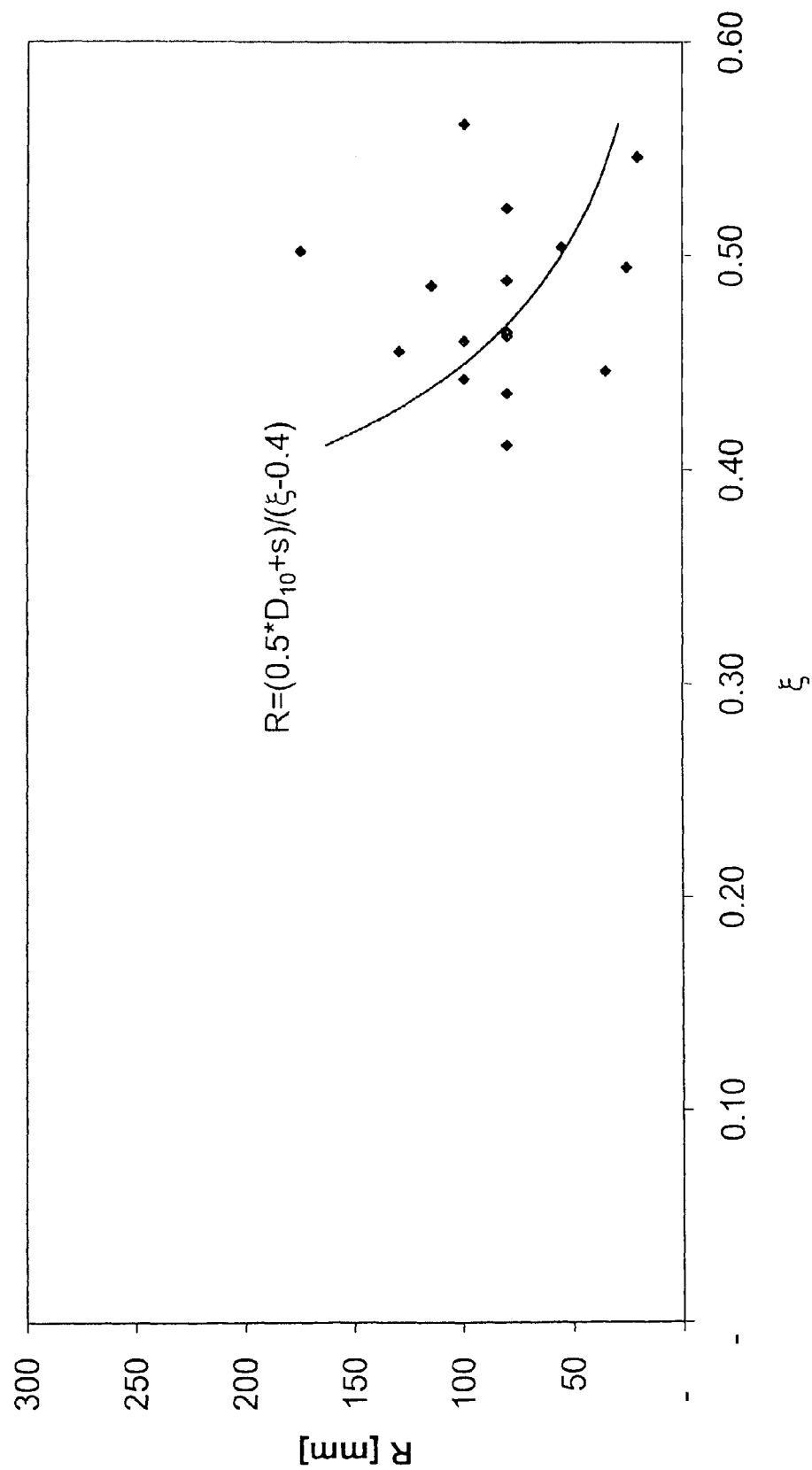
Figure 12:
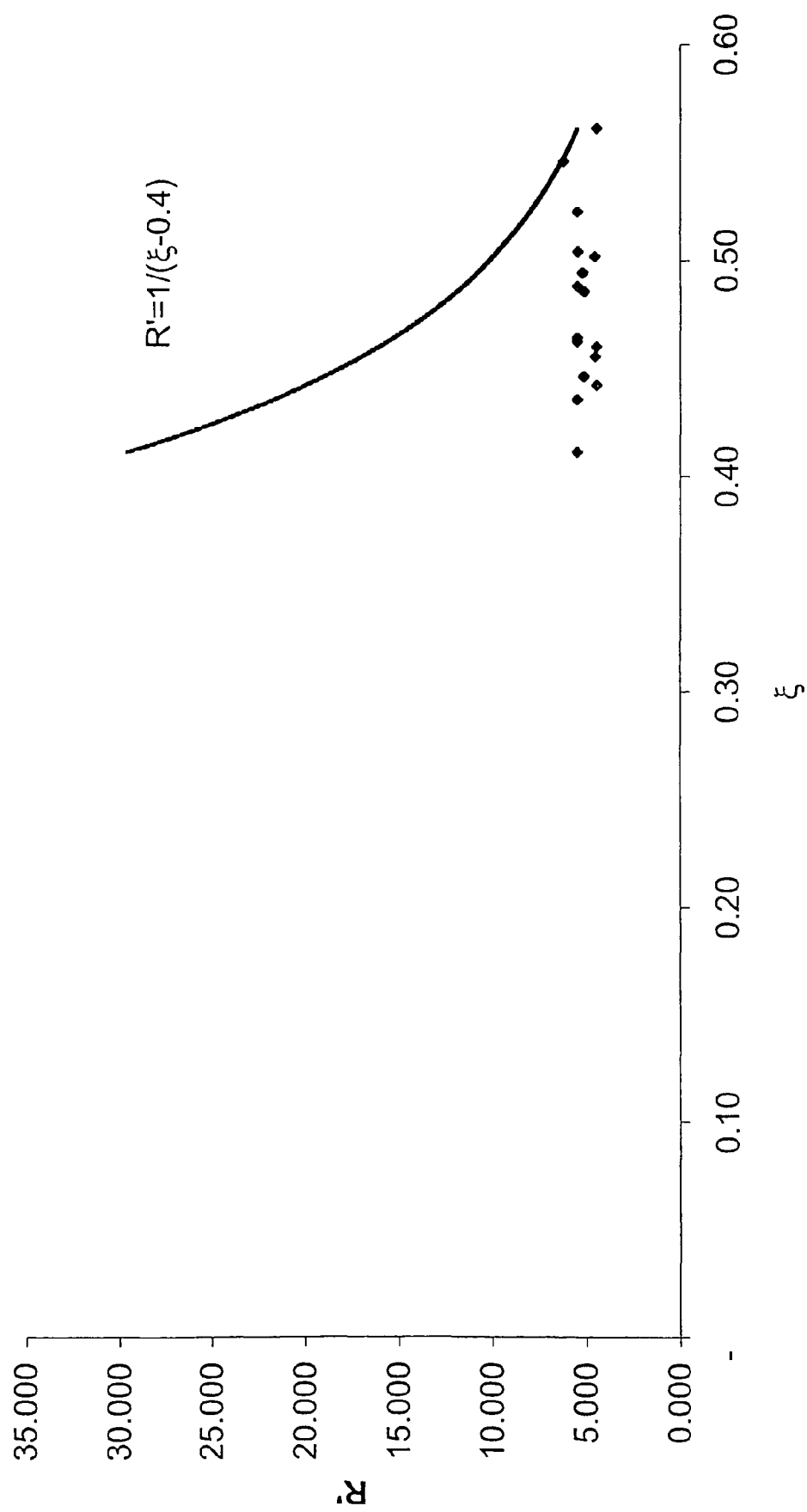
Figure 13:
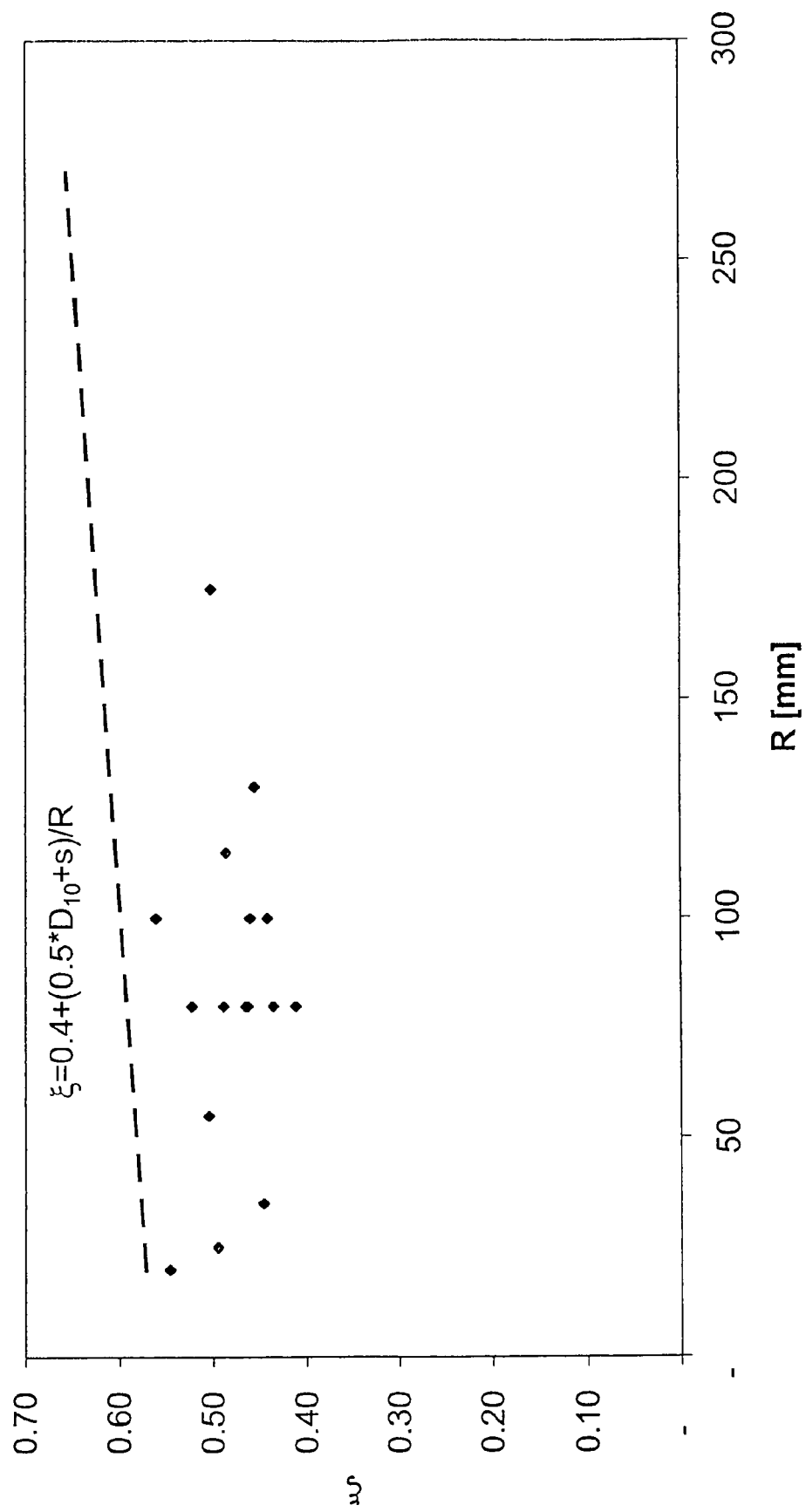
Figure 14:
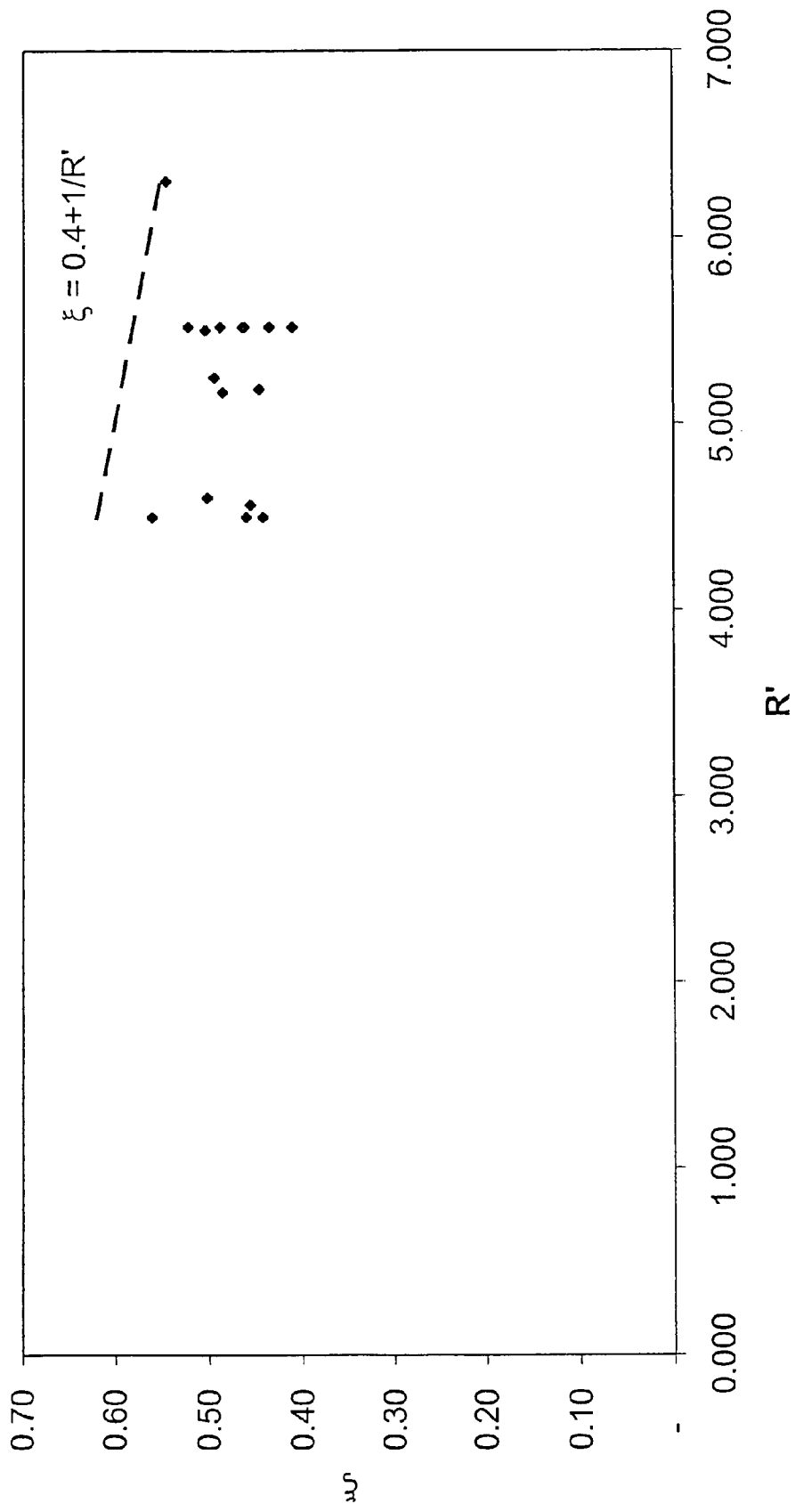

Through further investigations (from which individual results are shown by way of example in FIG. 10) on a large number of typical measuring transducer configurations with essentially V-shaped, curved measuring tubes, it has in particular come to light that for an optimization of the measuring transducer in the above sense, the first oscillation sensor of the sensor arrangement and the second oscillation sensor of the sensor arrangement are to be placed in the measuring transducer as a function of the aforementioned angle $\Theta$ (formed by the two straight segments of tube) in such a way that the aforementioned measuring-length to oscillatory-length ratio $\xi=L_{50}/L_{10}$ meets the condition $$\xi \leq 0.57 \cdot \left[1 - 0.1 \cdot \sin\left(\frac{\Theta}{2} - 30°\right)\right].$$

This is especially the case for measuring tubes with V-shaped, curved measuring tubes, for which the angle $\Theta$ is less than 100°.

Through further case investigations on measuring transducers in the case of which the angle $\Theta$ is greater than 100°, and especially greater than 115°, it has further been found for different sensor positions and measuring tube calibers, that, for a large number of traditional measuring transducer configurations with V-shaped measuring tubes, an optimal measuring-length to oscillatory-length ratio $\xi=L_{50}/L_{10}$ can be found, when the condition $\xi \leq 0.62$ (and especially the condition $\xi > 0.45$) is fulfilled.

Through further investigations (from which individual results are shown by way of example in FIGS. 11 through 14) on measuring tubes with essentially V-shaped measuring tubes, the above mentioned tube arc radius R of the arc-shaped tube segment has revealed itself as an additional variable for the dimensioning of a sensor position optimal in the above sense and, in association therewith, for an optimal measuring length or measuring-length to oscillatory-length ratio, $\xi$. In accordance therewith, it can additionally prove beneficial for the achievement of an in the above sense highest possible efficiency of the measuring tube, when, in the case mentioned, in which the measuring-length to oscillatory-length ratio $\xi=L_{50}/L_{10}$ amounts to less than 0.65 (and especially greater than 0.4), the tube arc radius R—as a function of the tube outer radius r (0.5 $D_{10}$+s) of the at least one measuring tube 10—fulfills the condition $$R \leq \frac{0.5 \cdot D_{10} + s}{\xi - 0.4}$$

or fulfills the condition $$R' \leq \frac{1}{\xi - 0.4}$$

or, conversely, the measuring-length to oscillatory-length ratio $\xi=L_{50}/L_{10}$ fulfills the condition $$\xi \leq \frac{0.5 \cdot D_{10} + s}{R} + 0.4$$

or $$\xi \leq \frac{1}{R'} + 0.4;$$

the latter in particular for the above-mentioned case, in which the arc-shaped tube segment is embodied in such a way, that its tube arc radius to tube outer radius ratio R' amounts to less than 60 and/or greater than 3.

Figure 15:
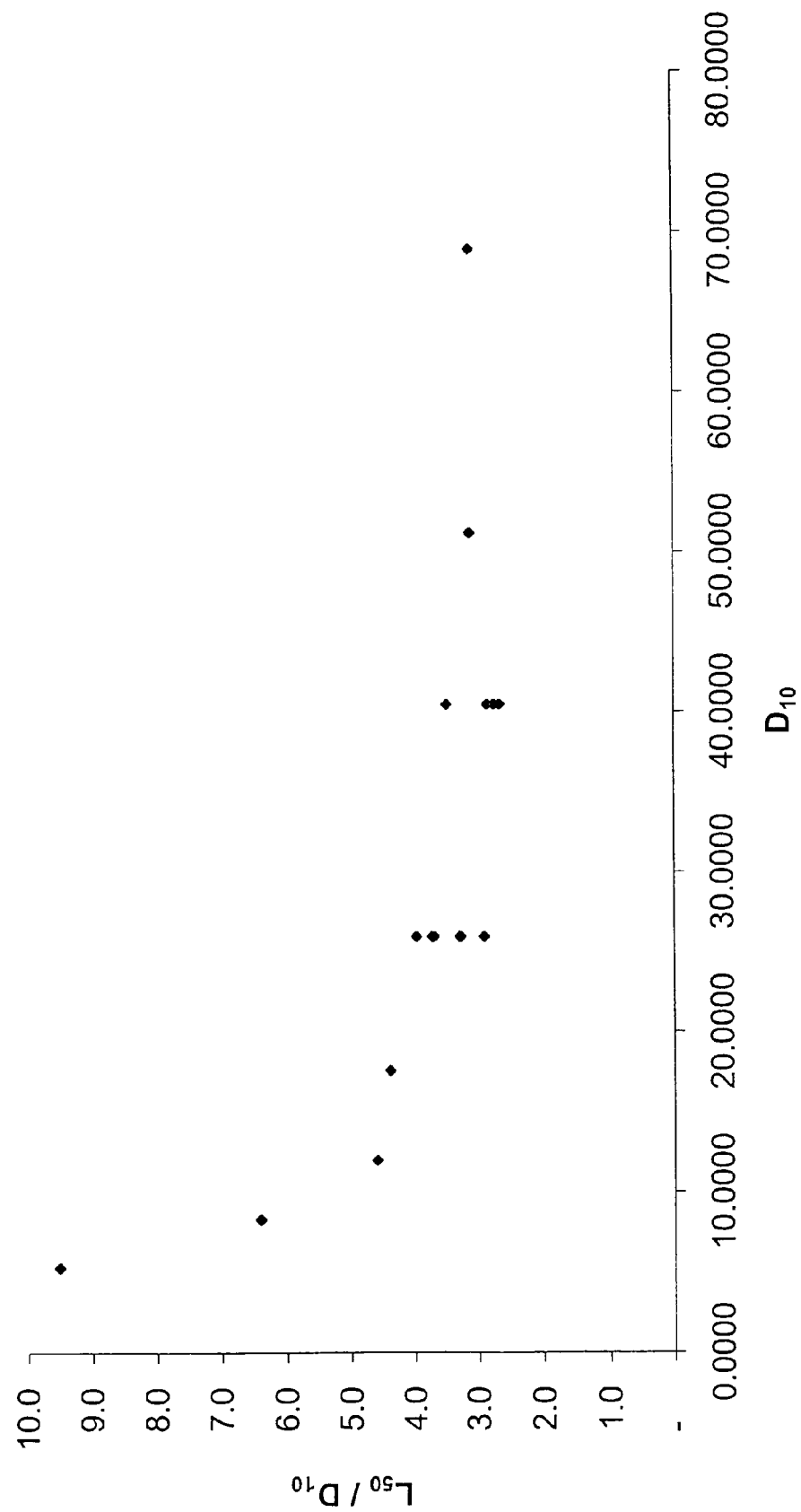
Figure 16:
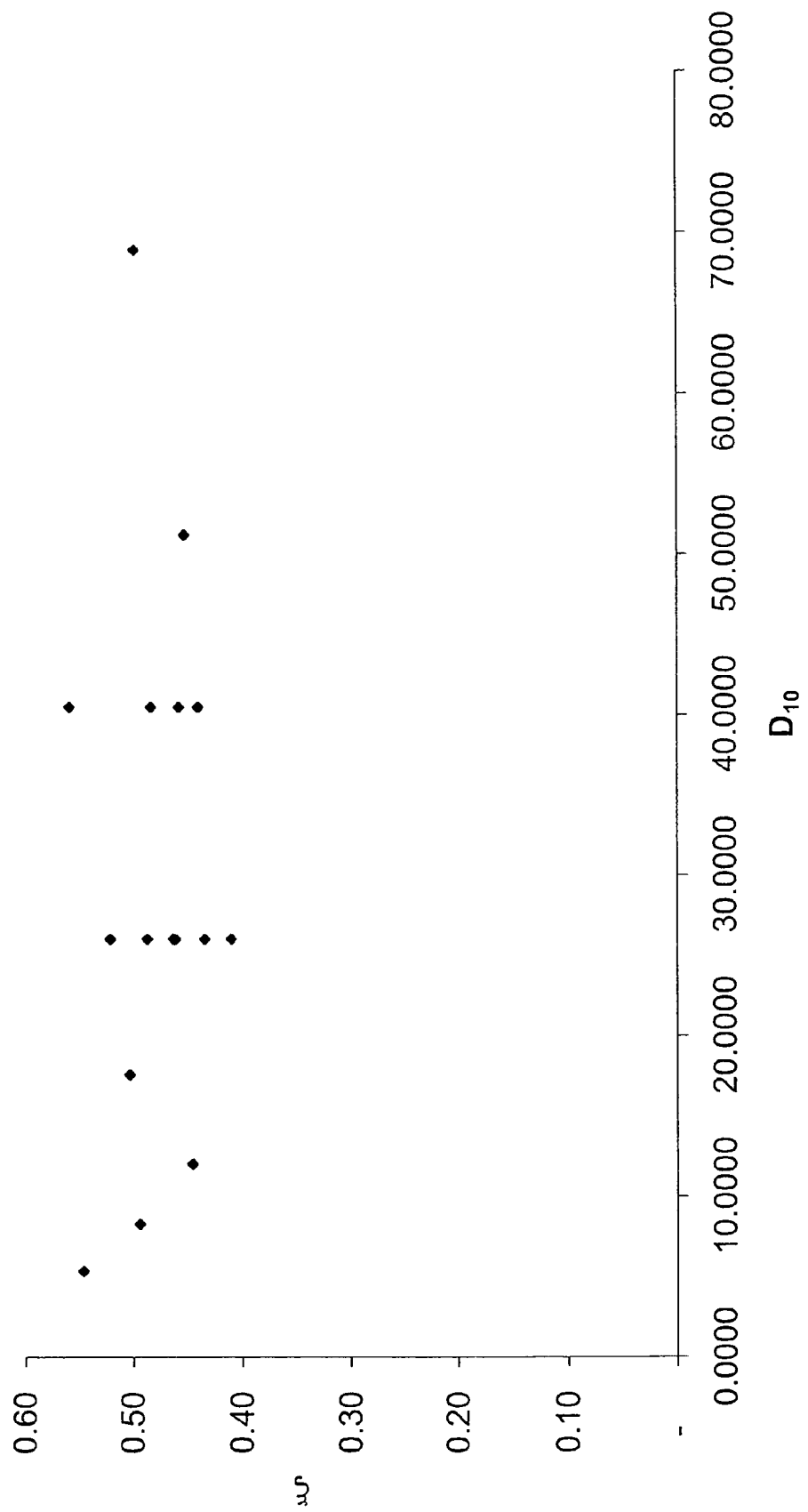
Figure 17:
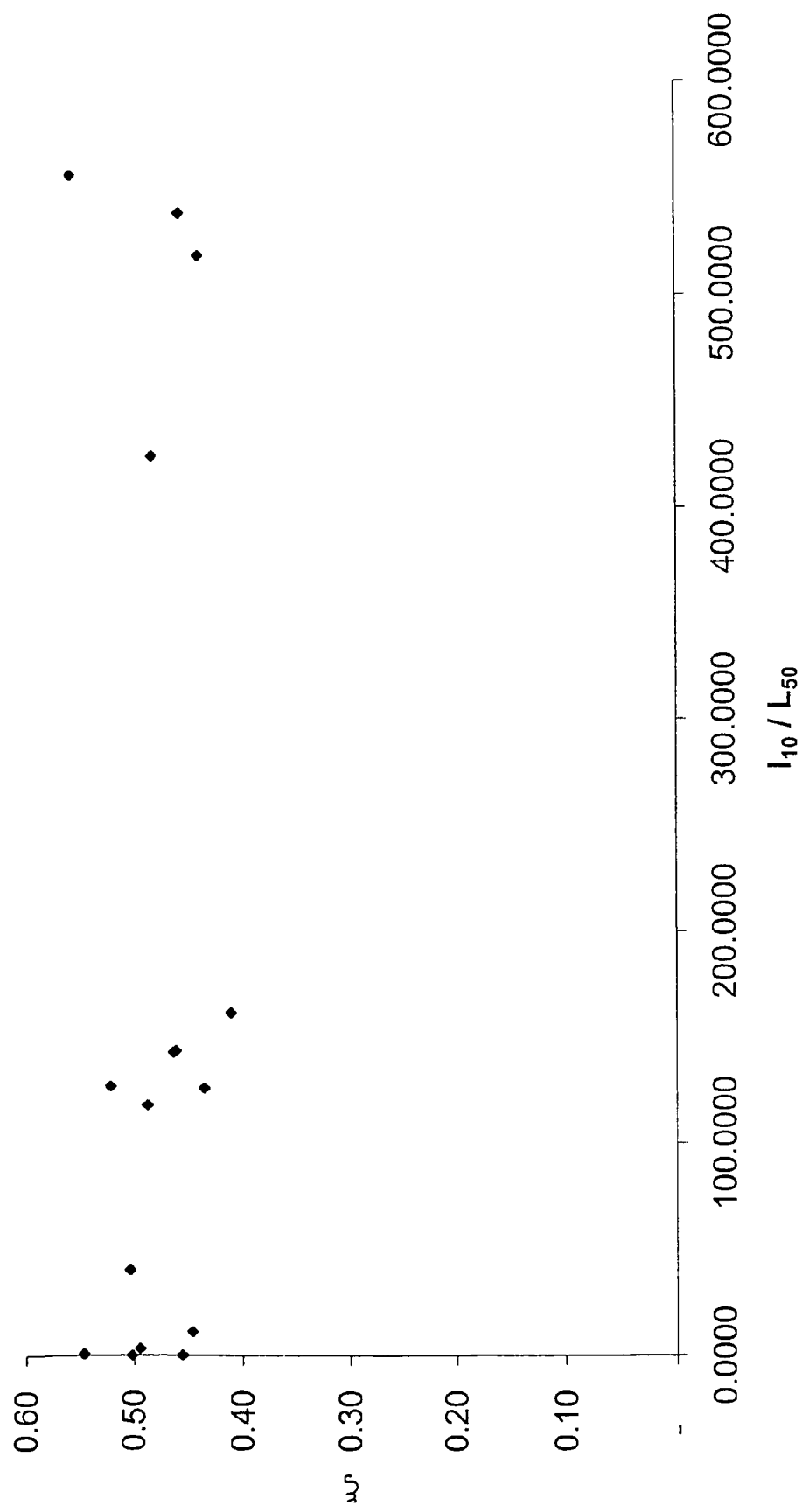

For further improvement of the previously indicated efficiency of the measuring transducer, or for maximizing the aforementioned optimizing function $\Re$, according to a further embodiment of the invention, the at least one measuring tube is dimensioned in such a way and the oscillation sensors are placed in the measuring transducer in such a way, that a measuring-length to caliber ratio $L_{50}/D_{10}$ of the measuring transducer (defined by a ratio of the measuring length $L_{50}$ of the measuring transducer to the caliber $D_{10}$ of the measuring tube) is smaller than 10 (especially smaller than 5); particularly in such a way (as is also evident from FIG. 15) that the caliber $D_{10}$ of the at least one measuring tube amounts to greater than 15 mm (especially greater than 20 mm), and that the measuring length $L_{50}$ of the measuring transducer corresponds to less than 55% of the oscillatory length $L_{10}$; or, in the case that the caliber $D_{10}$ of the measuring tube amounts to greater than 50 mm (especially greater than 60 mm), that measuring length $L_{50}$ of the measuring transducer corresponds to less than 65% of the oscillatory length $L_{10}$ (but especially greater than 40% of the oscillatory length $L_{10}$); this particularly for the case mentioned above, where the areal moment of inertia $I_{10}$ of the measuring tube amounts to 40 mm$^4$ or more, or where the measuring tube is shaped and dimensioned in such a way, and the oscillation sensors are positioned in such a way, that (as is evident from FIG. 17) an-areal-moment-of-inertia to measuring-length ratio $I_{10}/L_{50}$ of the measuring transducer (defined by a ratio of an areal moment of inertia $I_{10}$ of a cross-section of the measuring tube to measuring length $L_{50}$ of the measuring transducer) amounts to greater than 40 mm$^3$ (and especially greater than 100 mm$^3$).

With knowledge of the previously explained dimensioning rules for measuring tubes and sensor arrangements, those skilled in the art should be presented with no difficulties in optimizing measuring transducers of the sort described with the goal that, in the case of as small a maximum oscillation amplitude of the measuring tube as possible—or in the case of as small an electrical excitation power as possible—on one hand, the primary signals exhibit a high noise separation or a high signal-to-noise ratio, and, on the other hand, that the measuring transducer as a whole is, despite this, sufficiently sensitive to the primary measured variables to be registered, especially the mass flow rate and or the totaled mass flow.

The invention claimed is:

1. A vibration-type measuring transducer, comprising:
   at least one measuring tube for conveying a flowing medium, said at least one measuring tube extending with an oscillatory length between an inlet-side, first measuring tube end, and an outlet-side, second measuring tube end, and, said at least one measuring tube being at least sectionally curved and adapted to, oscillate about an oscillation axis, which is parallel to or coincides with an imagined connecting axis, which imaginarily connects said two measuring tubes ends;
   a sensor arrangement for registering oscillations at least of the at least one measuring tube, said sensor arrangement including a first oscillation sensor, which is arranged on said at least one measuring tube and which is adapted to deliver a first primary signal of the measuring transducer representing vibrations of said at least one measuring tube; and said sensor arrangement including a second oscillation sensor which is arranged on said at least one measuring tube spaced from said first measuring sensor and which is adapted to deliver a second primary signal of the measuring transducer representing vibrations of said at least one measuring tube, wherein:
   said at least one measuring tube includes an inlet-side, first straight tube segment, with an imaginary longitudinal axis exhibiting a direction vector pointing toward a first coupling zone, and an outlet-side, second straight tube segment, with an imaginary longitudinal axis exhibiting a direction vector pointing toward a second coupling zone, said first and said second straight segments of tube are arranged with respect to one another in such a way that said direction vector of the first straight tube segment and that said direction vector of the second straight tube segment intersect to form an angle, $\Theta$, in such a way that said angle, $\Theta$, exhibits a size of less than 170° and greater than 10°, and
   said first oscillation sensor of said sensor arrangement and said second oscillation sensor of said sensor arrangement are placed in the measuring transducer in such a way, that a measuring length of the measuring transducer corresponding to a length of a region extending between said first oscillation sensor and said second oscillation sensor corresponds to less than 65%, of the oscillatory length, and greater than 25%, of the oscillatory length.

2. The measuring transducer as claimed in claim 1, wherein:
   the at least one measuring tube is embodied in a partially arc-shaped fashion.

3. The measuring transducer as claimed in claim 1, wherein:
   said at least one measuring tube is embodied in an essentially V-shaped fashion, at least within the region extending between said first oscillation sensor and said second oscillation sensor.

4. The measuring transducer as claimed in claim 1, wherein:
   said at least one measuring tube exhibits a caliber that amounts to greater than 1 mm.

5. The measuring transducer as claimed in claim 4, wherein:
   said caliber of said at least one measuring tube amounts to greater than 50 mm and
   said measuring length corresponds to less than 65% of said oscillatory length.

6. The measuring transducer as claimed in claim 5, wherein:
   the caliber of said at least one measuring tube amounts to greater than 60 mm.

7. The measuring transducer as claimed in claim 5, wherein:
   the measuring length corresponds to greater than 40% of the oscillatory length.

8. The measuring transducer as claimed in claim 4, wherein:
said caliber of said at least one measuring tube amounts to greater than 15 mm and
said measuring length of the measuring transducer corresponds to less than 55% of said oscillatory length.

9. The measuring transducer as claimed in claim 8, wherein:
said caliber of said at least one measuring tube amounts to greater than 20 mm.

10. The measuring transducer as claimed in claim 8, wherein:
said caliber of said at least one measuring tube amounts less than 50 mm.

11. The measuring transducer as claimed in claim 4, wherein:
said at least one measuring tube end is dimensioned in such a way and the oscillation sensors placed in such a way, that a measuring-length to caliber ratio of the measuring transducer, defined by a ratio of said maximum measuring length of the measuring transducer to the caliber of said at least one measuring tube, is smaller than 10.

12. The measuring transducer as claimed in claim 11, wherein:
said at least one measuring tube end is dimensioned in such a way and the oscillation sensors placed in such a way, that said measuring-length to caliber ratio of the measuring transducer is smaller than 5.

13. The measuring transducer as claimed in claim 1, wherein:
said at least one measuring tube is shaped in such a way, that the angle $\Theta$ exhibits a size of less than 160° and/or greater than 20°.

14. The measuring transducer as claimed in claim 1, wherein:
said at least one measuring tube is shaped in such a way, that the angle $\Theta$ exhibits a size of less than 100°.

15. The measuring transducer as claimed in claim 14, wherein:
said first oscillation sensor of said sensor arrangement and said second oscillation sensor of said sensor arrangement are placed in the measuring transducer in such a way, that a measuring-length to oscillatory-length ratio, $\xi$, defined by a ratio of said measuring length to said oscillatory length, fulfils the condition $\xi \leq 0.6$.

16. The measuring transducer as claimed in claim 15, wherein:
said first oscillation sensor of said sensor arrangement and said second oscillation sensor of said sensor arrangement are placed in the measuring transducer in such a way, that the measuring-length to oscillatory-length ratio, $\xi$, defined by a ratio of said maximum measuring length to said oscillatory length, fulfils the condition $\xi > 0.35$.

17. The measuring transducer as claimed in claim 16, wherein:
said first oscillation sensor of said sensor arrangement and said second oscillation sensor of said sensor arrangement are placed in the measuring transducer in such a way, that the measuring-length to oscillatory-length ratio, $\xi$, defined by a ratio of said maximum measuring length to said oscillatory length, fulfils the condition:

$$\xi \leq 0.57 \cdot \left[1 - 0.1 \cdot \sin\left(\frac{\Theta}{2} - 30°\right)\right].$$

18. The measuring transducer as claimed in claim 1, wherein:
said at least one measuring tube is shaped in such a way, that the angle ($\Theta$) is greater than 50°.

19. The measuring transducer as claimed in claim 1, wherein:
said at least one measuring tube is shaped in such a way, that the angle $\Theta$ is greater than 100°.

20. The measuring transducer as claimed in claim 19, wherein:
said first oscillation sensor of said sensor arrangement and said second oscillation sensor of said sensor arrangement are placed in the measuring transducer in such a way, that the measuring-length to oscillatory-length ratio, $\xi$, defined by a ratio of said maximum measuring length to said oscillatory length, fulfils the condition $\xi \leq 0.62$.

21. The measuring transducer as claimed in claim 20, wherein:
said first oscillation sensor of said sensor arrangement and said second oscillation sensor of said sensor arrangement are placed in the measuring transducer in such a way, that the measuring-length to oscillatory-length ratio, $\xi$, defined by a ratio of said maximum measuring length to said oscillatory length, fulfils the condition $\xi > 0.45$.

22. The measuring transducer as claimed in claim 1, wherein:
said two straight tube segments are connected to each other by means of an arc-shaped tube segment.

23. The measuring transducer as claimed in claim 22, wherein:
said arc-shaped tube segment includes a middle tube arc radius which amounts to less than 500 mm and
said at least one measuring tube exhibits a tube wall thickness of less than 7 mm.

24. The measuring transducer as claimed in claim 23, wherein:
said at least one measuring tube is dimensioned in such a way and placed in the measuring transducer in such a way, that an areal-moment-of-inertia-to-measuring-length ratio of the measuring transducer defined by a ratio of an areal moment of inertia of a cross-section of said at least one measuring tube to a measuring length of the measuring transducer is greater than 40 mm$^3$ and that the areal moment of inertia of the cross section of said at least one measuring tube fulfills the condition $$I_{10} = \frac{\pi}{64} \cdot [D_{10}^4 - (D_{10} + s)^4].$$

25. The measuring transducer as claimed in claim 20, wherein:
said at least one tube is dimensioned in such a way, that said areal moment of inertia of said at least one measuring tube is at least 40 mm$^4$.

26. The measuring transducer as claimed in claim 24, wherein:
said at least one measuring tube is dimensioned in such a way, that said areal moment of inertia of said at least one measuring tube is greater than 150 mm$^4$.

27. The measuring transducer as claimed in claim 24, wherein:
    said at least one measuring tube is dimensioned in such a way and placed in the measuring transducer in such a way, that the areal-moment-of-inertia-to-measuring-length ratio of the measuring transducer is greater than 100 mm$^3$.

28. The measuring transducer as claimed in claim 23, wherein:
    wherein said first oscillation sensor of said sensor arrangement and said second oscillation sensor of said sensor arrangement are placed in the measuring transducer in such a way, that a measuring-length to oscillatory-length ratio, ξ, defined by a ratio of said maximum measuring length to said oscillatory length, amounts to less than 0.65; and
    said arc-shaped tube segment is embodied in such a way, that its tube arc radius fulfils the condition $$R \leq \frac{0.5 \cdot D_{10} + s}{\xi - 0.4}.$$

29. The measuring transducer as claimed in claim 23, wherein:
    said arc-shaped tube segment is embodied in such a way, that a tube arc radius to tube outer radius ratio amounts to less than 60 and/or greater than 3 and
    said first oscillation sensor of said sensor arrangement and said second oscillation sensor of said sensor arrangement are placed in the measuring tube in such a way that the measuring-length to oscillatory-length ratio, ξ, fulfils the condition $$\xi \leq \frac{1}{R'} + 0.4.$$

30. The measuring transducer as claimed in claim 29, wherein:
    said first oscillation sensor of said sensor arrangement and said second oscillation sensor of said sensor arrangement are placed in the measuring transducer in such a way, that the measuring-length to oscillatory-length ratio, ξ fulfils the condition ξ>0.4.

31. The measuring transducer as claimed in claim 23, wherein:
    said first oscillation sensor of said sensor arrangement and said second oscillation sensor of said sensor arrangement are placed in said at least one measuring tube is such a way that the measuring-length to oscillatory-length ratio, ξ amounts to less than 0.65; and
    said arc-shaped tube segment is embodied in such a way, that a tube arc radius to tube outer radius ratio fulfills the condition $$R' \leq \frac{1}{\xi - 0.4}.$$

32. The measuring transducer as claimed in claim 23, wherein:
    said arc-shaped tube segment is embodied in such a way, and said first oscillation sensor of said sensor arrangement and said second oscillation sensor of said sensor arrangement are placed in said at least one measuring tube is such a way, that the measuring-length to oscillatory-length ratio, ξ, fulfills the condition $$\xi \leq \frac{0.5 \cdot D_{10} + s}{R} + 0.4.$$

33. The measuring transducer as claimed in claim 32, wherein:
    said first oscillation sensor of said sensor arrangement and said second oscillation sensor of said sensor arrangement are placed in said at least one measuring tube is such a way that the measuring-length to oscillatory-length ratio, ξ fulfills the condition ξ>0.4.

34. The measuring transducer as claimed in claim 23, wherein:
    said at least one measuring tube is embodied in such a way, and said first oscillation sensor of said sensor arrangement and said second oscillation sensor of said sensor arrangement are placed in said at least one measuring tube in such a way, that the measuring transducer fulfills the condition $$\frac{L_{10}}{L_{50}} \cdot \left( \frac{0.5 \cdot D_{10} + s}{R} + 0.4 \right) \geq 1.$$

35. The measuring transducer as claimed in claim 34, wherein:
    said at least one measuring tube is embodied in such a way and said first oscillation sensor of said sensor arrangement and said second oscillation sensor of said sensor arrangement are placed in said at least one measuring tube is such a way, that the measuring transducer fulfills the condition $$\frac{L_{10}}{L_{50}} > 0.35.$$

36. The measuring transducer as claimed in claim 23, wherein:
    the middle tube arc radius of said arc-shaped tube segment amounts to less than 300 mm.

37. The measuring transducer as claimed in claim 23, wherein:
    the tube wall thickness of said at least one measuring tube is less than 3 mm.

38. The measuring transducer as claimed in claim 1, wherein:
    said first oscillation sensor and said second oscillation sensor are of equal construction to each other.

39. The measuring transducer as claimed in claim 1, further comprising:
    a counteroscillator, which, forming a first coupling zone, is affixed to said at least one measuring tube on the inlet side, and, forming a second coupling zone, is affixed to said at least one measuring tube on the outlet side, said counteroscillator which oscillates essentially with opposite phase to said at least one measuring tube and/or is parallel to said at least one measuring tube, wherein:
    said first coupling zone defines an inlet-side, first end of said at least one measuring tube, and said second coupling zone defines an outlet-side, second end of said at least one measuring tube.

40. The measuring transducer as claimed in claim 39, wherein:
both said first oscillation sensor and said second oscillation sensor are placed in the measuring transducer in such a way, that each of the oscillation sensors registers oscillations of said at least one measuring tube relative to said counteroscillator.

41. The measuring transducer as claimed in claim 39, wherein:
during operation, said at least one measuring tube and said counteroscillator oscillate at least at a shared oscillation frequency with opposite phase to one other; and/or
both said first primary signal and said second primary signal represent oscillatory movements of said at least one measuring tube relative to said counteroscillator.

42. The measuring transducer as claimed in claim 39, wherein:
said oscillation sensors register vibrations of said at least one measuring tube and said counteroscillator.

43. The measuring transducer as claimed in claim 1, wherein:
said first oscillation sensor is placed in the measuring transducer spaced as equally far from the half-length point of said at least one measuring tube as said second oscillation sensor is.

44. The measuring transducer as claimed in claim 1, wherein:
two measuring tubes are provided, which are mechanically connected to each other on the inlet side by means of a first coupling element forming a first coupling zone, and on the outlet side by means of a second coupling element forming a second coupling zone, said measuring tubes which oscillate essentially with opposite phase to one other and/or are parallel to one other and/or are equally embodied as regards shape and material; and
said first coupling zone defines an inlet side, first end of each of the measuring tubes, and said second coupling zone an outlet side, second end of each of said measuring tubes.

45. The measuring transducer as claimed in claim 44, wherein each of the two measuring tubes communicates on the inlet side with a first distributor element of the measuring transducer and on the outlet side with a second distributor element of the measuring transducer.

46. The measuring transducer as claimed in claim 44, wherein:
said two measuring tubes are adapted to oscillate at least at a shared oscillation frequency with opposite phase to one other; and/or
wherein both said first primary signal of the measuring transducer delivered by said first oscillation sensor and said second primary signal of the measuring transducer delivered by said second oscillation sensor represent oscillations of said measuring tubes relative to one other.

47. The measuring transducer as claimed in claim 1, further comprising:
an exciter mechanism including at least one oscillation exciter adapted to act on said at least one measuring tube for causing said at least one measuring tube to vibrate, in which it at least partially performs bending oscillations about the imagined oscillation axis.

48. The measuring transducer as claimed in claim 47, wherein:
said exciter mechanism is adapted to excite said at least one measuring tube in a wanted mode, in which said at least one measuring tube performs bending oscillations about the imagined oscillation axis.

49. The measuring transducer as claimed in claim 48, wherein:
each of the primary signals of the measuring transducer exhibits a signal component having a signal frequency corresponding to the bending oscillations of the wanted mode and/or corresponding to a resonance frequency of said at least one measuring tube.

50. The measuring tube as claimed in claim 47, wherein:
said first oscillation sensor is placed in the measuring transducer spaced as equally far from said at least one oscillation exciter as said second oscillation sensor is.

51. The measuring transducer as claimed in claim 47, wherein the at least one oscillation exciter-acts on said at least one measuring tube in the region of half of said oscillatory length.

52. The measuring transducer as claimed in claim 1, wherein:
said at least one measuring tube is made of metal.

53. The measuring transducer as claimed in claim 1, wherein:
said sensor arrangement exhibits no additional oscillation sensors beyond said first and second oscillation sensors.

54. The measuring transducer as claimed in claim 1, wherein:
said first oscillation sensor and said second oscillation sensor of said sensor arrangement are placed in the measuring transducer in such a way, that:
a sensitivity of the measuring transducer, with which a measured variable to be registered of a medium flowing through the measuring transducer is converted into a corresponding signal variable of said first and/or said second primary signal
relative to a theoretical sensitivity in the case of a maximum measuring length corresponding to said oscillatory length; and
a signal amplitude of said primary signals, which is actually achieved during operation, relative to a theoretical maximum possible amplitude at the site of maximum oscillatory amplitude fulfill the condition $$\frac{A_{ACT}}{A_{MAX}} \cdot \frac{S_{ACT}}{S_{MAX}} \stackrel{!}{=} \text{Max},$$

where
$A_{ACT}$=a single amplitude
$A_{MAX}$=theoretical maximum amplitude
$S_{ACT}$=the sensitivity of the measured variable
$S_{MAX}$=the maximum sensitivity of the measured variable.

55. The measuring device for flowable media said measuring device comprising:
a measuring transducer as claimed in claim 1, and a measuring device electronics electrically coupled with said measuring transducer for processing primary signals delivered by the measuring transducer and for producing measured values.

56. The measuring device as claimed in claim 55, wherein:
said measuring device electronics at least at times generates, both by means of said first primary signal and by means of said second primary signal a mass flow measured value representing an instantaneous mass flow rate of medium flowing through the measuring transducer.

57. The measuring device as claimed in claim 55, wherein:
during operation said measuring device electronics recurringly produces a phase difference value, which represents the phase difference, instantaneously existing between said first primary signal and said second primary signal.

58. The measuring device as claimed in claim 55, further comprising:
- a driver circuit which is electrically coupled with said measuring transducer, and which delivers an exciter signal which drives the measuring transducer's exciter mechanism.

59. The measuring device as claimed in claim 55, wherein: said measuring device electronics is electrically connectable with an external data processing system by means of a two-wire connection.

60. The measuring device as claimed in claim 55, wherein: said evaluating circuit, by means of at least one of said two primary signals, at least at times, generates a density measured value, which represents an instantaneous density, of medium flowing through said measuring transducer.

61. The measuring device as claimed in claim 55, wherein: said evaluating circuit, by means of at least one of said two primary signals, at least at times generates a viscosity measured value, which represents an instantaneous viscosity, of medium flowing through said measuring transducer.

62. The method for measuring a mass flow and/or a density and/or a viscosity and/or a pressure of a medium flowing in a process line said method comprising: using a measuring device as claimed in claim 55.

63. The measuring transducer as claimed in claim 1, wherein:
- a region of said at least one measuring tube, extending between said first oscillation sensor and said second oscillation sensor, is embodied in a partially arc-shaped fashion.

64. The measuring transducer as claimed in claim 1, wherein: said at least one measuring tube exhibits a caliber that amounts to greater than 5 mm.

65. The measuring transducer as claimed in claim 1, wherein:
- said first oscillation sensor of said sensor arrangement and said second oscillation sensor of said sensor arrangement are placed in the measuring transducer in such a way, that said measuring length of the measuring transducer corresponds to less than 55% of the oscillatory length.

66. The measuring transducer as claimed in claim 1, wherein:
- said first oscillation sensor of said sensor arrangement and said second oscillation sensor of said sensor arrangement are placed in the measuring transducer in such a way, that said measuring length of the measuring transducer corresponds to greater than 30% of the oscillatory length.

* * * * *